(12) United States Patent
Schierholz et al.

(10) Patent No.: US 8,192,987 B2
(45) Date of Patent: Jun. 5, 2012

(54) HUMAN DENTAL FOLLICLE STEM CELLS AND METHODS FOR OBTAINING

(75) Inventors: Jörg Schierholz, Bergisch Gladbach (DE); Hans-Florian Zeilhofer, Basel (DE); Karl-Heinz Hoffmann, Munich (DE); Christian Morsczexk, Essen (DE); Norbert Brenner, Bonn (DE)

(73) Assignee: TissueDent GmbH & Co. KG, Bonn (DE)

( * ) Notice: Subject to any disclaimer, the term of this patent is extended or adjusted under 35 U.S.C. 154(b) by 47 days.

(21) Appl. No.: 12/068,695

(22) Filed: Feb. 11, 2008

(65) Prior Publication Data
US 2009/0035282 A1    Feb. 5, 2009

Related U.S. Application Data

(63) Continuation of application No. 10/497,206, filed as application No. PCT/EP03/01131 on Feb. 5, 2003, now abandoned.

(60) Provisional application No. 60/354,152, filed on Feb. 6, 2002.

(51) Int. Cl.
C12N 5/02 (2006.01)

(52) U.S. Cl. ......... 435/395; 435/377; 435/384; 435/366

(58) Field of Classification Search .................. None
See application file for complete search history.

(56) References Cited

U.S. PATENT DOCUMENTS
5,885,829 A   3/1999   Mooney et al.

FOREIGN PATENT DOCUMENTS
WO   WO 01 21767 A   3/2001
WO   WO 02/07679     1/2002

OTHER PUBLICATIONS

D'Errico et al. Models for the Study of Cementogenesis. Connective Tissue Research. 1995, vol. 33, Nos. 1-3, pp. 9-17.*
Thesleff et al. Changes in the Distribution of Tenascin During Tooth Development, Development, 1987, vol. 101, pp. 289-296.*
Sakata et al. Expression of Osteoprotegerin (Osteoclastogenesis Inhibitory Factor) in Cultures of HUman Dental Mesenchymal Cells and Epithelial CellsJ. Bone Mineral Metab., 1999, vol. 14, 1486-1492.*
Goseki-Sone et al. Expression of mRNA Encoding Tissue-Nonspecifiic Alkaline Phosphatase in Humen Dental Tissues. Calcified Tissue International, 1999, vol. 64, pp. 160-162.*
Aziz et al. Engraftment and Migration of Human Bone Marrow Stromal Cells Implanted in the Brains of Albino Rats—Simlarities to Astrocyte Grafts. Proc. Natl. Acad. Sci., 1998, vol. 95, pp. 3908-3913.*
Cheng et al. Expression of Bone Matrix Proteins During Dexamethasone-Induced Mineralization of Human Bone Marrow Stromal Cells. J Cellular Biochemistry, 1996, vol. 61, pp. 182-193.*
Peng et al. Mesenchymal Stem Cells and Tooth Engineering International J Oral Science, 2009, col. 1, pp. 6-12.*
Avots et al., "Plasticity of hematopoietic stem cells and cellular memory", Immunological Reviews, 187 (2002), 9-21.
Gronthos et al., "Postnatal human dental pulp stem cells (DPSCs) in vitro and in vivo", Proceedings of the Natioal Academy of Sciences of USA, 97:25 (2000), 13625-30.
Handa et al., "Progenitor cells from dental follicle are able to form cemetum matrix in vivo", Connective Tissue Research, 43:2/3 (2002), 406-408.
Harada et al., "Localization of putative stem cells in dental epithelium and their association with Notch and FGF signaling", Journal of Cell Biology, 147:1 (1999), 105-20.
Krebsbach et al., "Dental and skeletal stem cells: potential cellular therapeutics for craniofacial regeneration", Journal of Dental Education, 66:6 (2002), 766-73.
Nakashima et al., Induction of dental pulp stem cell differentiation into odontoblasts by electroporation-mediated gene delivery of growth/differentiation fadctor 11 (Gdfll), Gene Therapy, 9:12 (2002), 814-18.
Pera et al., "Isolation and characterization of a multpotent clone of human embryonal carcinoma cells", Differentiation 42:1 (1989), 10-23.
Shi et al., "Comparison of human dental pulp and bone marrow stromal stem cells by cDNA microarray analysis", Bone 29:6 (2001), 532-39.
Watt et al., "Out of Eden: Stem cells and their niches", American Association for the Advancement of Sciences, 287:5457 (2000), 1427-30.
Yen et al., Expert Opinion in Biological Therapy, 6:9-16, 2006.
Handa et al., 31:606-611, 2002.
Wise et al., Cell Tissue Research, 267: 483-492, 1992.
Larjava et al., Biochemical Journal, 284: 267-274, 1992.
Pittenger et al., Science, 284: 143-147, 1999.
Wise et al., Archives of Oral Biology, 37: 471-478, 1992.
Morsczeck et al. In Vitro Differentiation of Human Dental Follicle Cells with Dexamethasone and Insulin. Cell Bio. International. 2005, vol. 29, pp. 567-575.
Morsczeck et al. Isolation of Precursor Cells (PCs) from Human Dental Follicle of Wisdom Teeth. Matrix Biol. 2005, vol., 24.pp. 155-165.
D'Errico et al., Models for the Study of Cementogenesis. Connective Tissue Research. 1995, vol. 33, Nos. 1-3, pp. 9-17.
Brivanlou et al. Setting Standards for Human Embryonic Stem Cells. Science. May 9, 2003, vol. 300, 913-916.
Hakki et al. Journal of Periodontology, 72:679-687, 2001. Abstract only.

* cited by examiner

*Primary Examiner* — Deborah Crouch
(74) *Attorney, Agent, or Firm* — Jacobson Holman PLLC

(57) ABSTRACT

A stem cell which is obtainable from the non-embryonic tissue isolated from the dental follicle of tooth or wisdom tooth which are able to differentiate into a periodontal ligament like membrane structure.

11 Claims, 11 Drawing Sheets

α

β

SEQUENCE LISTING

```
<160> NUMBER OF SEQ ID NOS: 50

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
cgtcttcacc accatggaga                                                  20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
cggccatcac gccacagttt                                                  20

<210> SEQ ID NO 3
<211> LENGTH: 21
<212> TYPE: DNA
<213> ORGANISM: Artificial
<220> FEATURE:
<223> OTHER INFORMATION: primer

<400> SEQUENCE: 3
aggccctcaa ggtttccaag g                                                21

<210> SEQ ID NO 4
<211> LENGTH: 21
<212> TYPE: DNA
<213> ORGANISM: Artificial
<220> FEATURE:
<223> OTHER INFORMATION: primer

<400> SEQUENCE: 4
```

```
ccagaccatv gtgtccccta a                                         21

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
tggtgttgga gccgctgcca                                           20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
ctcagcacta gaatctgtcc                                           20

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
ggagacagag gcttcactgg                                           20

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
actgctcgca tcatgttctg                                           20

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
gtgcagtatc atgccctgtg                                           20

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
aacaggtctg ggttttgtgc                                           20

<210> SEQ ID NO 11
<211> LENGTH: 20
<212> TYPE: DNA
<213> ORGANISM: Artificial
<220> FEATURE:
```

<223> OTHER INFORMATION: primer

<400> SEQUENCE: 11
acccgactca gtttcaccag                                           20

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
tcagccttag acgcctcaat                                           20

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
gccctgacca ctccagttta                                           20

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
ggagtcctgg atttccttcc                                           20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
cagtctgacc agcgtgaaaa                                           20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
ggccatccaa atctgtccta                                           20

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
tgaagcctag cctgtcacct                                           20

<210> SEQ ID NO 18

```
<211> LENGTH: 20
<212> TYPE: DNA
<213> ORGANISM: Artificial
<220> FEATURE:
<223> OTHER INFORMATION: primer

<400> SEQUENCE: 18
cgcacagctg gaggtcttat                                                  20

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
ggtattggca gttggaggaa                                                  20

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
acatttgccg cttggataac                                                  20

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
gggacctcta cgaggaggag                                                  20

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
cgcattgtca acatcctgtc                                                  20

<210> SEQ ID NO 23
<211> LENGTH: 21
<212> TYPE: DNA
<213> ORGANISM: Artificial
<220> FEATURE:
<223> OTHER INFORMATION: primer

<400> SEQUENCE: 23
ggcaaggaat tcaaacctga c                                                21

<210> SEQ ID NO 24
<211> LENGTH: 21
<212> TYPE: DNA
<213> ORGANISM: Artificial
<220> FEATURE:
<223> OTHER INFORMATION: primer

<400> SEQUENCE: 24
```

```
catcacggct ggtctctctt c                                              21

<210> SEQ ID NO 25
<211> LENGTH: 21
<212> TYPE: DNA
<213> ORGANISM: Artificial
<220> FEATURE:
<223> OTHER INFORMATION: primer

<400> SEQUENCE: 25
aacgggaagg agtttaagga g                                              21

<210> SEQ ID NO 26
<211> LENGTH: 21
<212> TYPE: DNA
<213> ORGANISM: Artificial
<220> FEATURE:
<223> OTHER INFORMATION: primer

<400> SEQUENCE: 26
ggagctattt atccccgagt g                                              21

<210> SEQ ID NO 27
<211> LENGTH: 21
<212> TYPE: DNA
<213> ORGANISM: Artificial
<220> FEATURE:
<223> OTHER INFORMATION: primer

<400> SEQUENCE: 27
tggcagaact gtcaaccatg c                                              21

<210> SEQ ID NO 28
<211> LENGTH: 21
<212> TYPE: DNA
<213> ORGANISM: Artificial
<220> FEATURE:
<223> OTHER INFORMATION: primer

<400> SEQUENCE: 28
aacgggaagg agtttaagca g                                              21

<210> SEQ ID NO 29
<211> LENGTH: 21
<212> TYPE: DNA
<213> ORGANISM: Artificial
<220> FEATURE:
<223> OTHER INFORMATION: primer

<400> SEQUENCE: 29
aacggcaggg agttccgcgg c                                              21

<210> SEQ ID NO 30
<211> LENGTH: 24
<212> TYPE: DNA
<213> ORGANISM: Artificial
<220> FEATURE:
<223> OTHER INFORMATION: primer

<400> SEQUENCE: 30
cttggggccc gtgaacacgc agcc                                           24

<210> SEQ ID NO 31
<211> LENGTH: 21
<212> TYPE: DNA
<213> ORGANISM: Artificial
<220> FEATURE:
```

-continued

<223> OTHER INFORMATION: primer

<400> SEQUENCE: 31
aacggcaggg agttccgcgg c                                              21

<210> SEQ ID NO 32
<211> LENGTH: 21
<212> TYPE: DNA
<213> ORGANISM: Artificial
<220> FEATURE:
<223> OTHER INFORMATION: primer

<400> SEQUENCE: 32
gcagcaccag ccacgcagag t                                              21

<210> SEQ ID NO 33
<211> LENGTH: 21
<212> TYPE: DNA
<213> ORGANISM: Artificial
<220> FEATURE:
<223> OTHER INFORMATION: primer

<400> SEQUENCE: 33
gatggacagg cctttcatgg g                                              21

<210> SEQ ID NO 34
<211> LENGTH: 24
<212> TYPE: DNA
<213> ORGANISM: Artificial
<220> FEATURE:
<223> OTHER INFORMATION: primer

<400> SEQUENCE: 34
tgctgcggtc catgtggggt cctc                                           24

<210> SEQ ID NO 35
<211> LENGTH: 22
<212> TYPE: DNA
<213> ORGANISM: Artificial
<220> FEATURE:
<223> OTHER INFORMATION: primer

<400> SEQUENCE: 35
tgatatgcat gcttttcttc tg                                             22

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
tggttgatgc ccttacatga                                                20

<210> SEQ ID NO 37
<211> LENGTH: 22
<212> TYPE: DNA
<213> ORGANISM: Artificial
<220> FEATURE:
<223> OTHER INFORMATION: primer

<400> SEQUENCE: 37
aaaaggcgag agctgttttg gc                                             22

<210> SEQ ID NO 38

```
<211> LENGTH: 22
<212> TYPE: DNA
<213> ORGANISM: Artificial
<220> FEATURE:
<223> OTHER INFORMATION: primer

<400> SEQUENCE: 38
taaaccagcg tcccagctac ca                                              22

<210> SEQ ID NO 39
<211> LENGTH: 24
<212> TYPE: DNA
<213> ORGANISM: Artificial
<220> FEATURE:
<223> OTHER INFORMATION: primer

<400> SEQUENCE: 39
ctatggagag gacgccacgc ctgg                                            24

<210> SEQ ID NO 40
<211> LENGTH: 23
<212> TYPE: DNA
<213> ORGANISM: Artificial
<220> FEATURE:
<223> OTHER INFORMATION: primer

<400> SEQUENCE: 40
catagccatc gtagccttgt cct                                             23

<210> SEQ ID NO 41
<211> LENGTH: 16
<212> TYPE: DNA
<213> ORGANISM: Artificial
<220> FEATURE:
<223> OTHER INFORMATION: primer

<400> SEQUENCE: 41
catgagagcc ctcaca                                                     16

<210> SEQ ID NO 42
<211> LENGTH: 17
<212> TYPE: DNA
<213> ORGANISM: Artificial
<220> FEATURE:
<223> OTHER INFORMATION: primer

<400> SEQUENCE: 42
agagcgacac cctagac                                                    17

<210> SEQ ID NO 43
<211> LENGTH: 21
<212> TYPE: DNA
<213> ORGANISM: Artificial
<220> FEATURE:
<223> OTHER INFORMATION: primer

<400> SEQUENCE: 43
atactgacat ggatcctgcc a                                               21

<210> SEQ ID NO 44
<211> LENGTH: 21
<212> TYPE: DNA
<213> ORGANISM: Artificial
<220> FEATURE:
<223> OTHER INFORMATION: primer

<400> SEQUENCE: 44
```

-continued

| tccaactgcc acggtcctga t | 21 |

```
<210> SEQ ID NO 45
<211> LENGTH: 20
<212> TYPE: DNA
<213> ORGANISM: Artificial
<220> FEATURE:
<223> OTHER INFORMATION: primer

<400> SEQUENCE: 45
```

| ctctccgtgc tgttctctcc | 20 |

```
<210> SEQ ID NO 46
<211> LENGTH: 20
<212> TYPE: DNA
<213> ORGANISM: Artificial
<220> FEATURE:
<223> OTHER INFORMATION: primer

<400> SEQUENCE: 46
```

| cgggccagat gttgtacttt | 20 |

```
<210> SEQ ID NO 47
<211> LENGTH: 24
<212> TYPE: DNA
<213> ORGANISM: Artificial
<220> FEATURE:
<223> OTHER INFORMATION: primer

<400> SEQUENCE: 47
```

| tggagcttca gaagctcaac acca | 24 |

```
<210> SEQ ID NO 48
<211> LENGTH: 24
<212> TYPE: DNA
<213> ORGANISM: Artificial
<220> FEATURE:
<223> OTHER INFORMATION: primer

<400> SEQUENCE: 48
```

| atctcgttgt ctgagtacca gtcc | 24 |

```
<210> SEQ ID NO 49
<211> LENGTH: 22
<212> TYPE: DNA
<213> ORGANISM: Artificial
<220> FEATURE:
<223> OTHER INFORMATION: primer

<400> SEQUENCE: 49
```

| cctaaagaaa atgaagataa tt | 22 |

```
<210> SEQ ID NO 50
<211> LENGTH: 22
<212> TYPE: DNA
<213> ORGANISM: Artificial
<220> FEATURE:
<223> OTHER INFORMATION: primer

<400> SEQUENCE: 50
```

| tagaaaaact cttccctcct ac | 22 |

HUMAN DENTAL FOLLICLE STEM CELLS AND METHODS FOR OBTAINING

Figure 1:
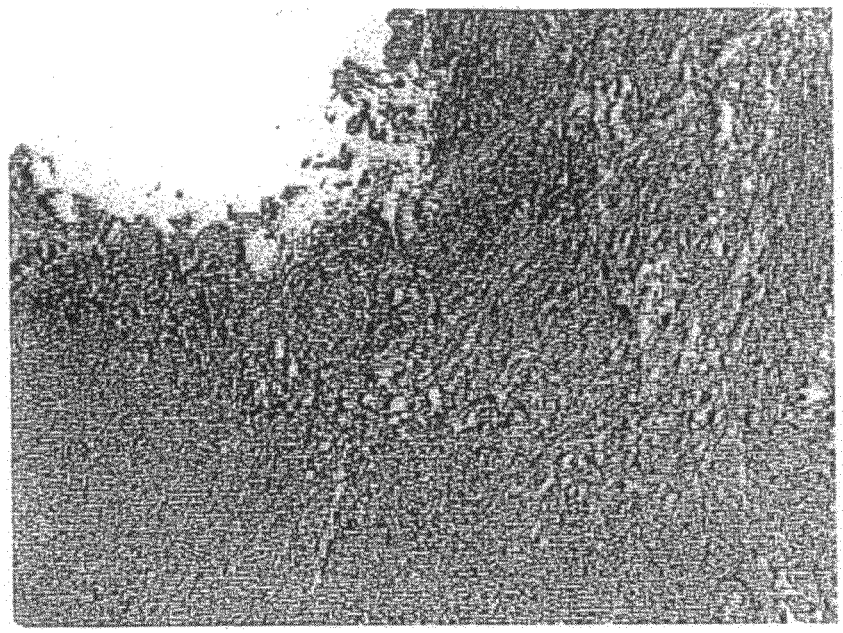
Figure 1:
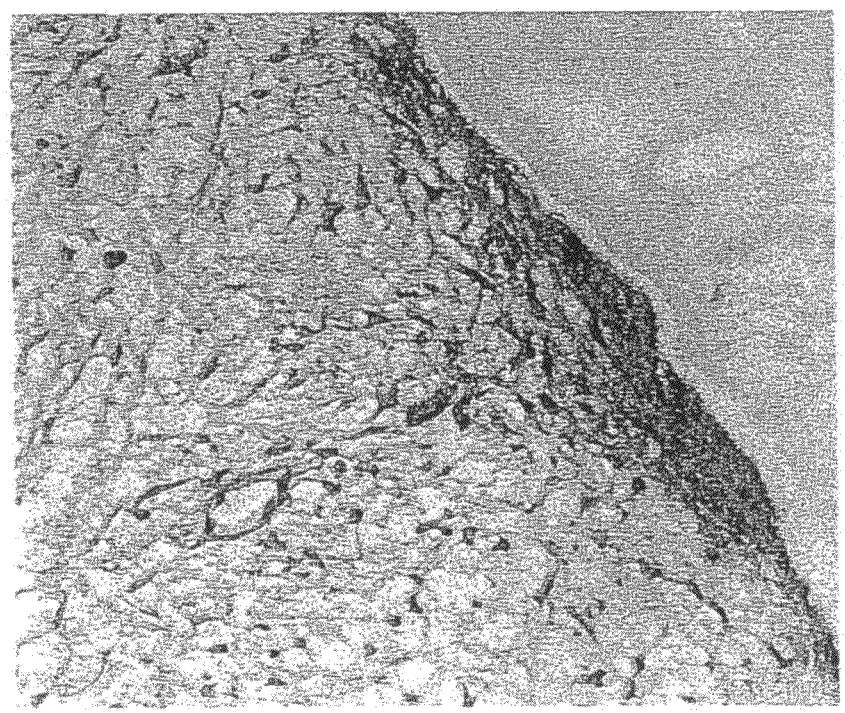

This is a continuation of Ser. No. 10/497,206, filed, Jan. 10, 2005 now abandoned, which is a 371 of PCT/EP03/01131, filed Feb. 5, 2003, which claims the benefit of U.S. Provisional Application No. 60/354,152, filed Feb. 6, 2002.

This invention relates generally to pluripotent stem cells, including embryonic-like pluripotent stem cells derived from teeth. The invention also relates to uses of the stem cells for tissue engineering in cell or tissue transplantation, in gene therapy, and in identifying, assaying or screening with respect to cell-cell interactions, lineage commitment, development genes and growth or differentiation factors.

BACKGROUND OF THE INVENTION

Stem Cell Location

Any tissue or organ in stasis or undergoing repair and having a connective tissue compartment, has resident populations of mesenchymal stem cells. Organs, tissues and their associated connective tissue components assayed to date include whole embryo, whole foetus, skeletal muscle, dermis, fat, tendon, ligament, perichondrium, periosteum, heart, aorta, endocardium, myocardium, epicardium, large arteries and veins, granulation tissue, peripheral nerves, peripheral ganglia, spinal cord, dura, leptomeninges, trachea, oesophagus, stomach, small intestine, large intestine, liver, spleen, pancreas, parietal peritoneum, visceral peritoneum, parietal pleura, visceral pleura, urinary bladder, gall bladder, kidney associated connective tissues and bone marrow.

Recently, stem cells from dental pulp have been isolated by Gronthos et al. 2000, Shi et al. WO 02/07679. Sharpe (WO 01/60981) claimed the production of tooth progenitor cells from embryonic stem cells or adult stem cells or tissue culture. Moreover, Yelick and colleagues (U.S. patent application: 20020119180) claimed the method and the production of a biological tooth from third molar tooth germ (Young et al. 2002). They removed and discarded immature tooth cusps and used cells of remaining enamel and pulp organ tissues for tooth engineering.

The invention enables the skilled person to identify, separate and to build teeth like and teeth related organs and tissues by tissue engineering. The surprising advantage of the invention is the preferred use of follicle cells of wisdom teeth, which are routinely extracted in adults and children. Thus, a source of stem cells was developed which freely available even for any adult patients. In contrast to the described stem cells above, these said stem cells are differentiable into a periodontal ligament related biological membrane.

Definition of Stem Cells

A Stem Cell can replicate itself and produce cells that take on more specialized functions. The function adopted by the more differentiated daughter cells and their progeny is commonly referred to as the developmental potential, or potency, of the stem cells. Stem cells that give rise to only one type differentiated cell are termed unipotent. In common usage, the relative terms oligopotent, multipotent, and pluripotent represent an increase in the number of differentiated types from new to many or most. A totipotent cell is one that can generate the totality of cell types that can comprise the organism. In practice, these few terms poorly describe a continuum of possibilities.

The ability to form a wide variety of cell types makes pluripotent stem cells a promising resource for tissue engineering and transplantation. Through the use of enrichment, selection, expression, and sorting technologies, in vitro differentiation of stem cells will certainly contribute to future transplantation therapies.

Multipotent stem cells can be cultured from a number of foetal and adult sources. Perhaps the best known source is bone marrow, which contains both haematopoietic stem cells (Civin et al., 1984) and mesenchymal stem cells (Pittenger et al., 1999). Neural stem cells have also been cultured from the ependymal cells lining the brain ventricles (Johansson et al., 1999a). It is likely that of the many lineage-restricted stem cell populations that exist in vivo, some will be amenable to in vitro growth and analysis.

The organization of the embryo into three layers roughly corresponds to the organization of the adult, with gut on the inside, epidermis on the outside, and connective tissue in between. The endoderm is the source of the epithelial linings of the respiratory passages and gastrointestinal tract and gives rise to the pharynx, oesophagus, stomach, intestine and to many associated glands, including salivary glands, liver, pancreas and lungs. The mesoderm gives rise to smooth muscular coats, connective tissues, and vessels associated with the tissues and organs; mesoderm also forms most of the cardiovascular system and is the source of blood cells and bone marrow, the skeleton, striated muscles, and the reproductive and excretory organs. Ectoderm will form the epidermis (epidermal layer of the skin), the sense organs, and the entire nervous system, including brain, spinal cord, and all the outlying components of the nervous system.

Reserve stem cells include progenitor stem cells and pluripotent stem cells. Progenitor cells precursor stem cells, immediate stem cells, and forming or -blast cells, e.g., myoblasts, adipoblasts, chondroblasts, etc.) are lineage-committed. Unipotent stem cells will form tissues restricted to a single lineage (such as the myogenic, fibrogenic, adipogenic, chondrogenic, osteogenic lineages, etc.). Bipotent stem cells will form tissues belonging to two lineages (such as the chondro-osteogenic, adipo-fibroblastic lineages, etc.). Tripotent stem cells will form tissues belonging to three lineages (such as chondro-osteo-adipogenic lineage, etc.). Multipotent stem cells will form multiple cell types within a lineage (such as the hematopoietic lineage). Progenitor stem cells will form tissues limited to their lineage, regardless of the inductive agent that may bedded to the medium. They can remain quiescent. Lineage-committed progenitor cells are capable of self-replication but have a limited life-span (approximately 50-70 cell doublings) before programmed cell senescence occurs. They can also be stimulated by various growth factors to proliferate. If activated to differentiate, these cells require progression factors (i.e., insulin, insulin-like growth factor-1, and insulin-like growth factor-11) to stimulate phenotypic expression. In contrast, pluripotent cells are lineage-uncommitted, i.e., they are not committed to any particular tissue lineage. They can remain quiescent. They can also be stimulated.

Examples of progenitor and pluripotent stem cells from the mesodermal germ layer include the unipotent myosatellite myoblasts of muscle; the unipotent adipoblast cells of adipose tissue); the unipotent chondrogenic cells and osteogenic cells of the perichondrium and periosteum, respectively; the bipotent adipofibroblasts of adipose tissue (Vierck et al., 1996); the bipotent chondrogenic/osteogenic stem cells of marrow); the tripotent hondrogenic/osteogenic/adipogenic stem cells of marrow (Pittenger et al., 1999); the multipotent hematopoietic stem cells of marrow; the multipotent cadiogenic/hematopoietic/endotheliogenic cells of marrow; and the pluripotent mesenchymal stem cells of the connective tissues Pluripotent mesenchymal stem cells and methods of isolation and use thereof are described in U.S. Pat. No. 5,827,735, issued Oct. 27, 1998.

Pluripotent mesenchymal stem cells can be utilized for the replacement of potentially multiple tissues of mesodermal origin (i.e., bone, cartilage, muscle, adipose tissue, vasculature, tendons, ligaments and hematopoietic), such tissues generated, for instance, ex vivo with specific morphogenetic proteins and growth factors to recreate the lost tissues. The recreated tissues would then be transplanted to repair the site of tissue loss. An alternative strategy could be to provide pluripotent stem cells, as cellular compositions or incorporated, for instance, into matrices, transplant into the area of need, and allow endogenous morphogenetic proteins and growth factors to induce the pluripotent stem cells to recreate the missing histoarchitecture of the tissue. This approach is exemplified in U.S. Pat. No. 5,903,934 which is incorporated herein in its entirety, which describes the implanting of pluripotent mesenchymal stem cells into a polymeric carrier, to provide differentiation into cartilage and/or bone at a site for cartilage repair.

SUMMARY OF THE INVENTION

The formation of tissues and organs occurs naturally in early normal human development, however, the ability to regenerate most human tissues damaged or lost due to trauma or disease is substantially diminished in adults. One object of the invention is to solve the problem of teeth- and teeth-related tissue substitution. Another object is to provide a source of regenerative cells from adults.

Surprisingly, stem-cells in wisdom teeth were found, which have the potential for extended self renewal of teeth, periodontium and related tissues such as bones. The present invention relates to pluripotent stem cells, particularly to pluripotent, multipotent, tri-bi-and unipotent stem cells.

The invention further relates to methods of purifying pluripotent embryonic-like stem cells and to compositions, cultures and clones thereof. The present invention also relates to a method of transplanting the pluripotent stem cells of the present invention in a mammalian host, such as human, comprising introducing the stem cells, into the host. The invention further relates to methods of in vivo administration of a protein or gene of interest comprising transfecting a pluripotent stem cell with a construct comprising DNA which encodes a protein of interest and then introducing the stem cell into the host where the protein or gene of interest is expressed. The present invention also relates to methods of producing mesodermal, endodermal or ectodermal lineage-committed cells by culturing or transplantation of the pluripotent stem cells or segregation these germ layers through progressive lineage-commitment into progenitor (multipotent, tripotent, bipotent and eventually unipotent) lineages of the present invention.

The present invention also relates to engineering of teeth and teeth surrounding tissue such as paradentin or bone, vessels or nerves related to teeth.

The invention relates also to the development of a stem cell bank for teeth or teeth derived tissues teeth derived tissues, as well as the development of membrane-like meso/endodermal matrices which can be used for a wide range of regenerative medicine.

Two general strategies have been adopted for the creation of new teeth-related tissue:
(1) Isolated stem cells or cell substitutes applied to the area of tissue deficiency or compromise.
(2) Cells placed on or within matrices are implanted and become incorporated into the body combined with tissue-inducing substances, that rely on growth factors to regulate specific cells to a committed pattern of growth resulting in tissue regeneration, and methods to deliver these substances to their targets.

The approach for engineering teeth and related tissues is exemplified within the present invention.

BRIEF DESCRIPTIONS OF THE DRAWINGS

Figure 2:
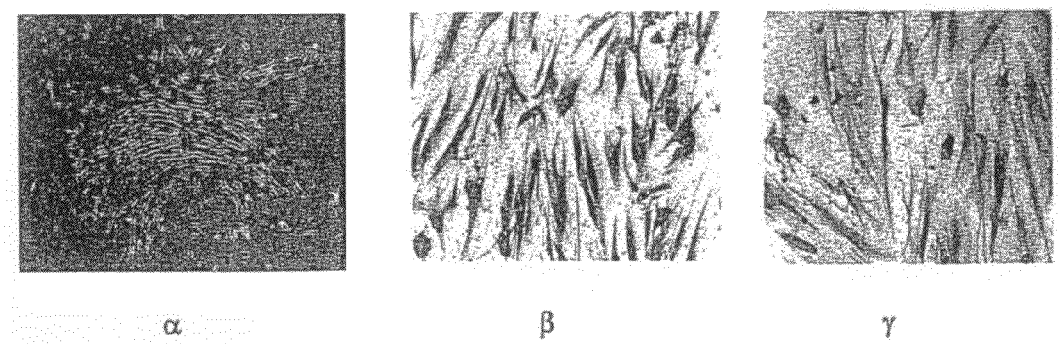

FIG. 1 and FIG. 2 photographically depict slices of dental follicle tissue.

Figure 3A:
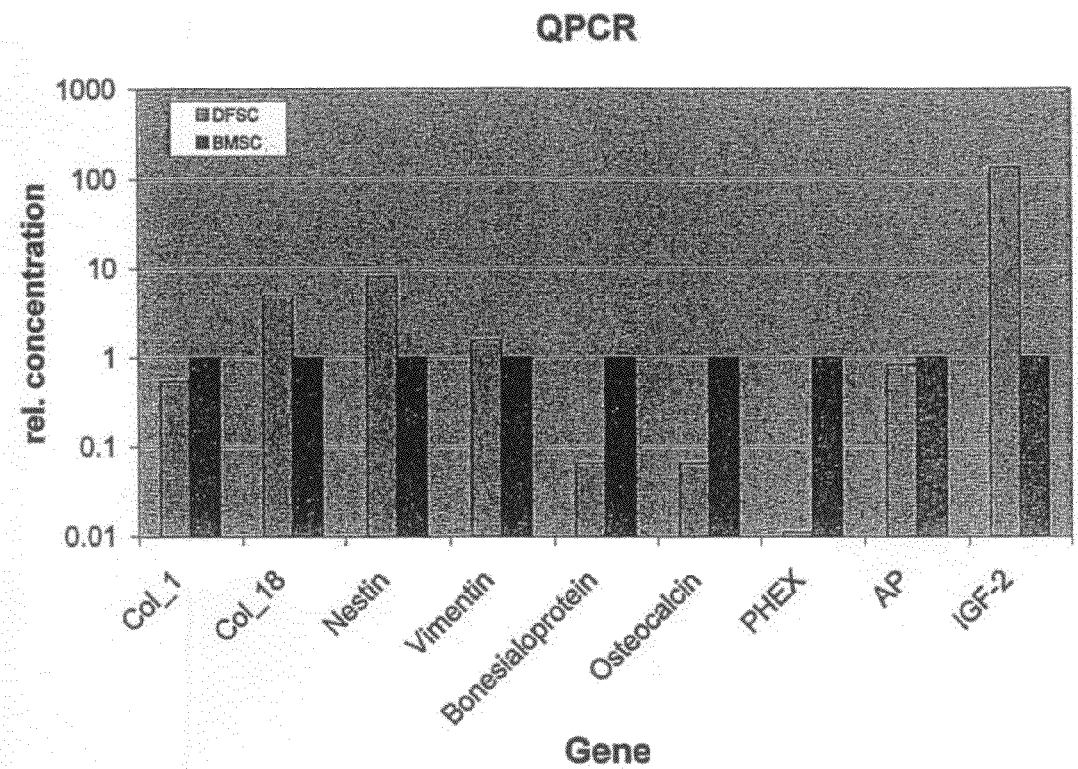

FIG. 3a graphically depicts QPCR for relative concentration values, with cultured BMSC and DFSC.

Figure 3B:
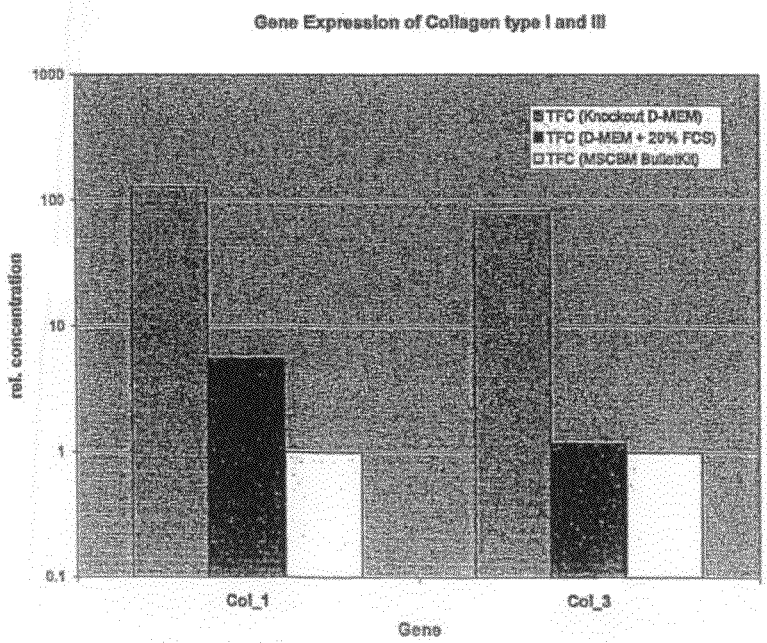

FIG. 3b graphically depicts QPCR for relative concentration values, with cultured BMSC and DFSC.

Figure 4:
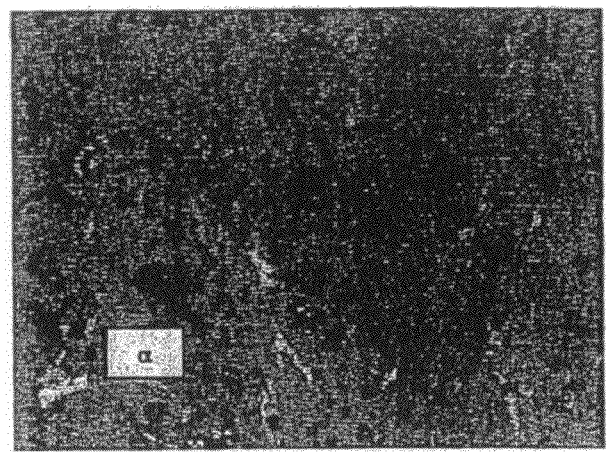
Figure 4:
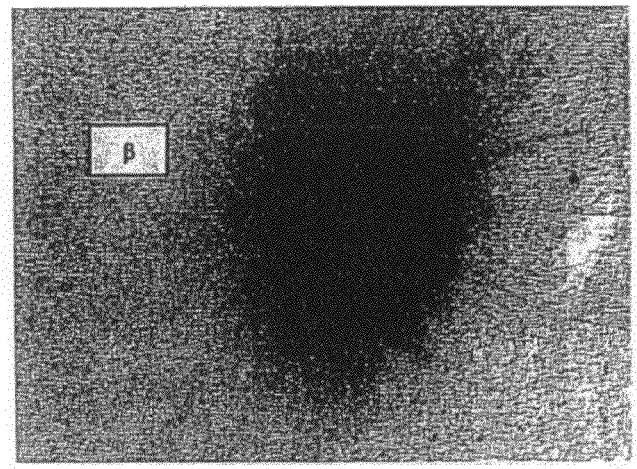
Figure 4:
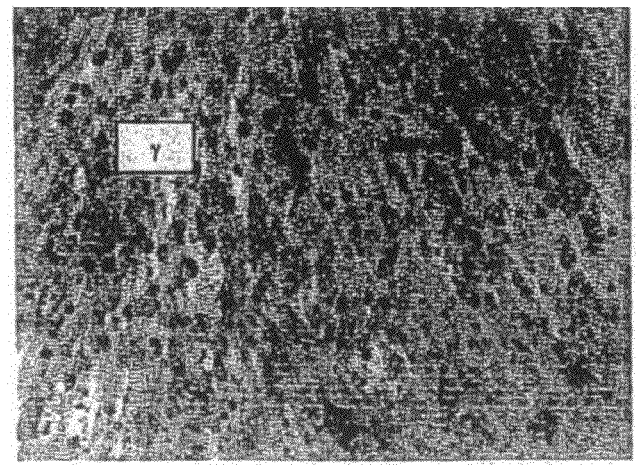

FIG. 4 photographically depicts differentiation of DFSC and BMSC in vitro.

Figure 5:
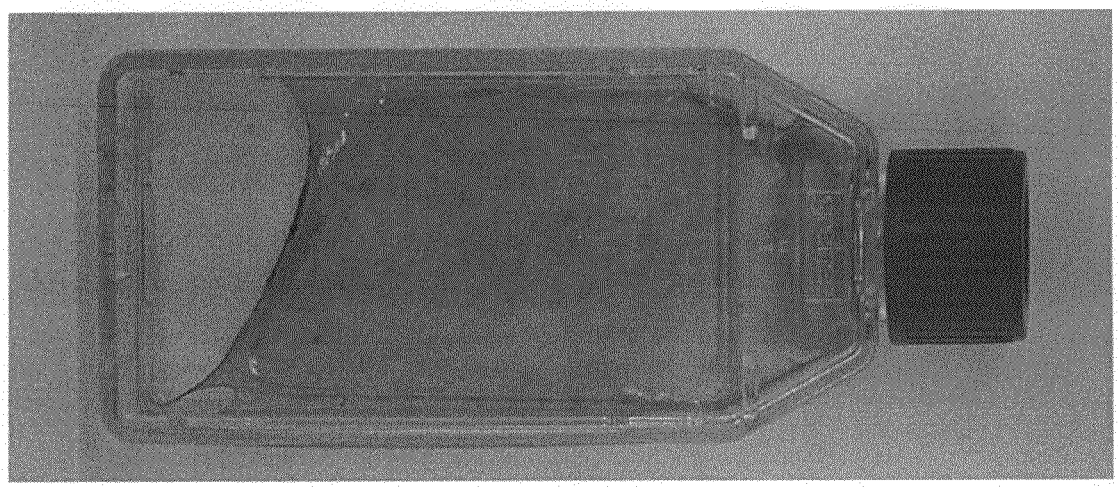

FIG. 5 photographically depicts a layer of cultured DFSCs in a culture bottle.

Figure 6:
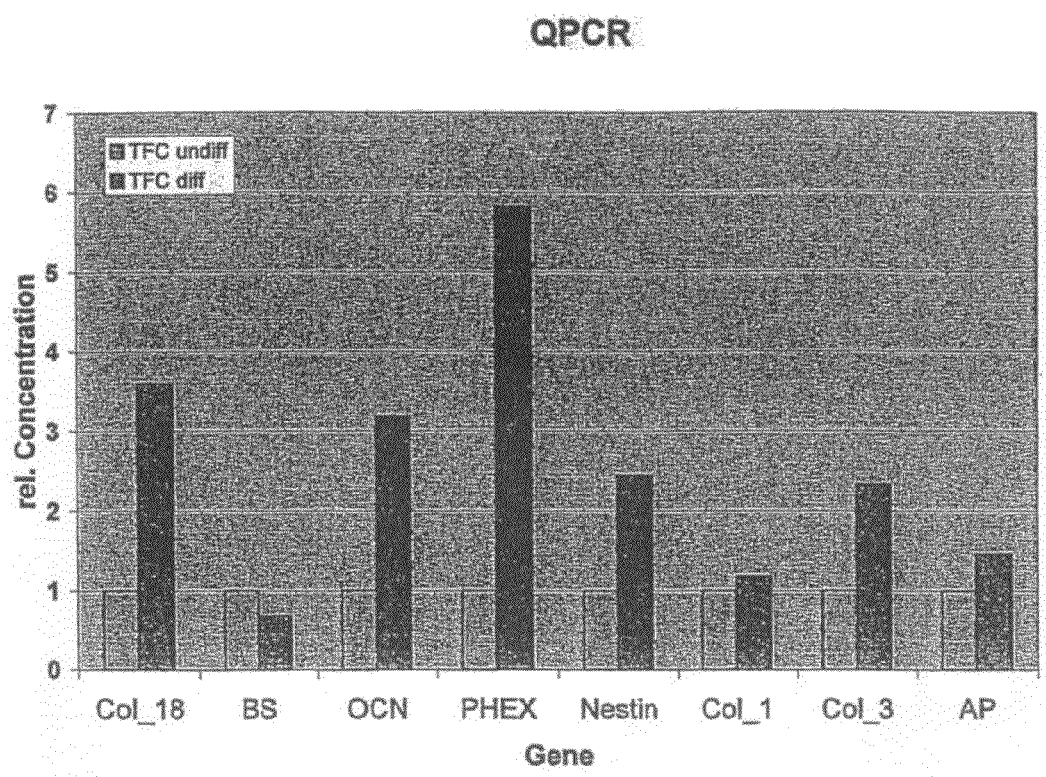

FIG. 6 graphically depicts QPCR with cDNA from DFSCs cultured in media with and without dexamethason.

Figure 7:
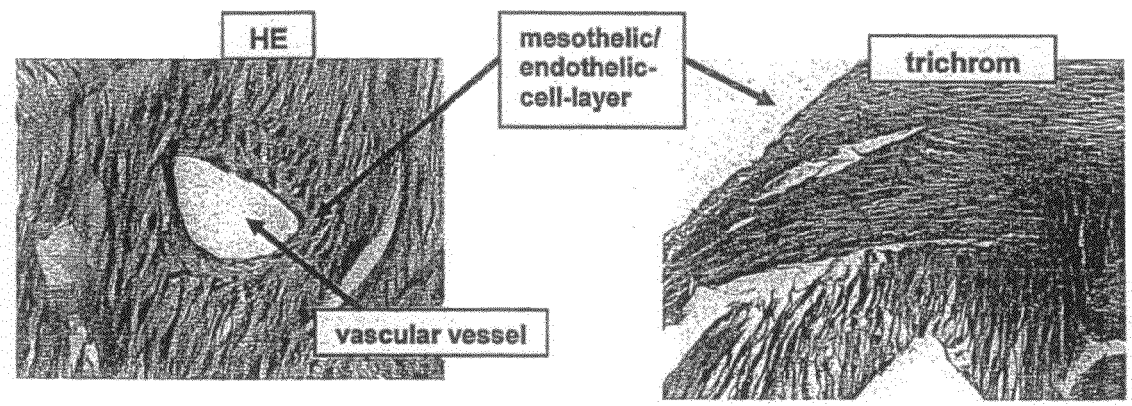

FIG. 7 photographically depicts HE- and trichrom-stainings with FTM-slices.

Figure 8:
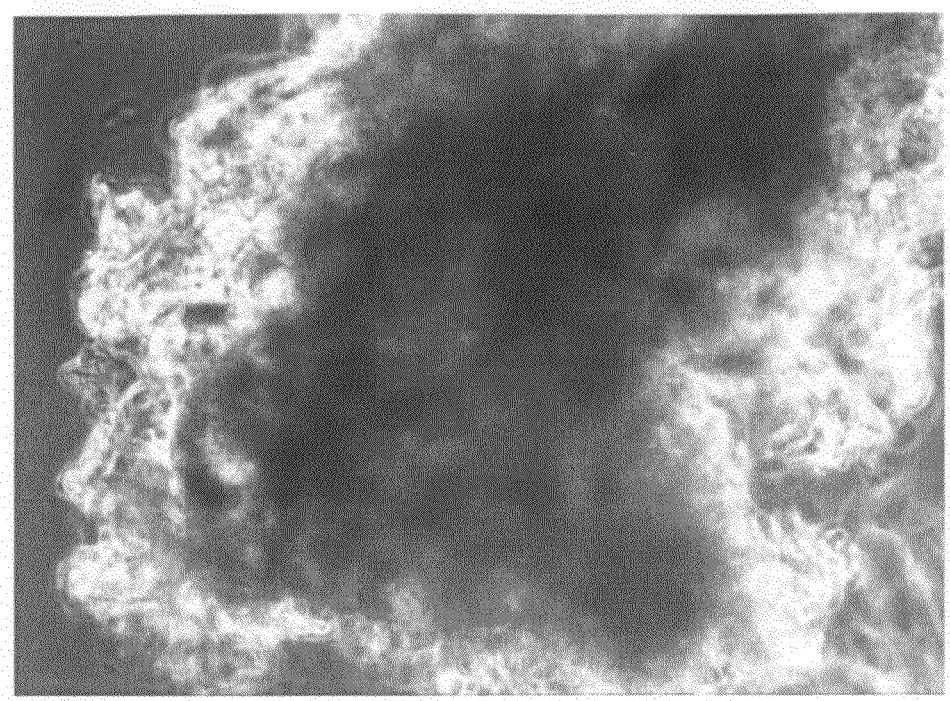

FIG. 8 photographically depicts a fixed section of scaffold with cultured stem cells.

Figure 9:
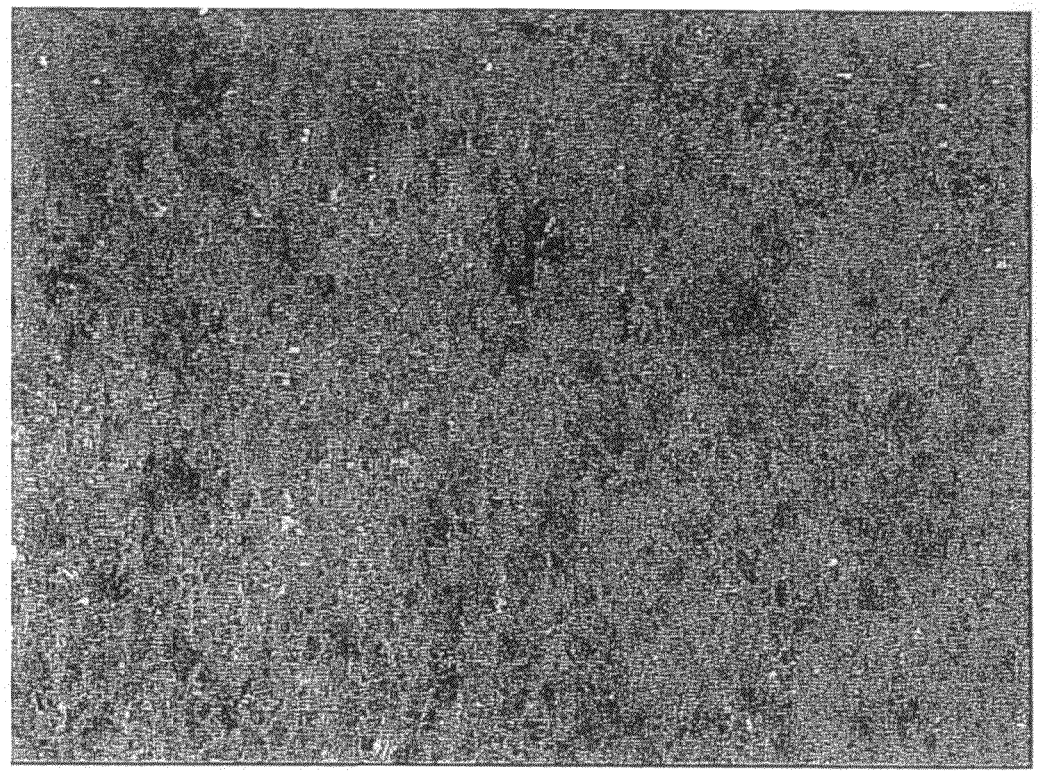

FIG. 9 photographically depicts pore structure of PLLA-polymer.

Figure 10:
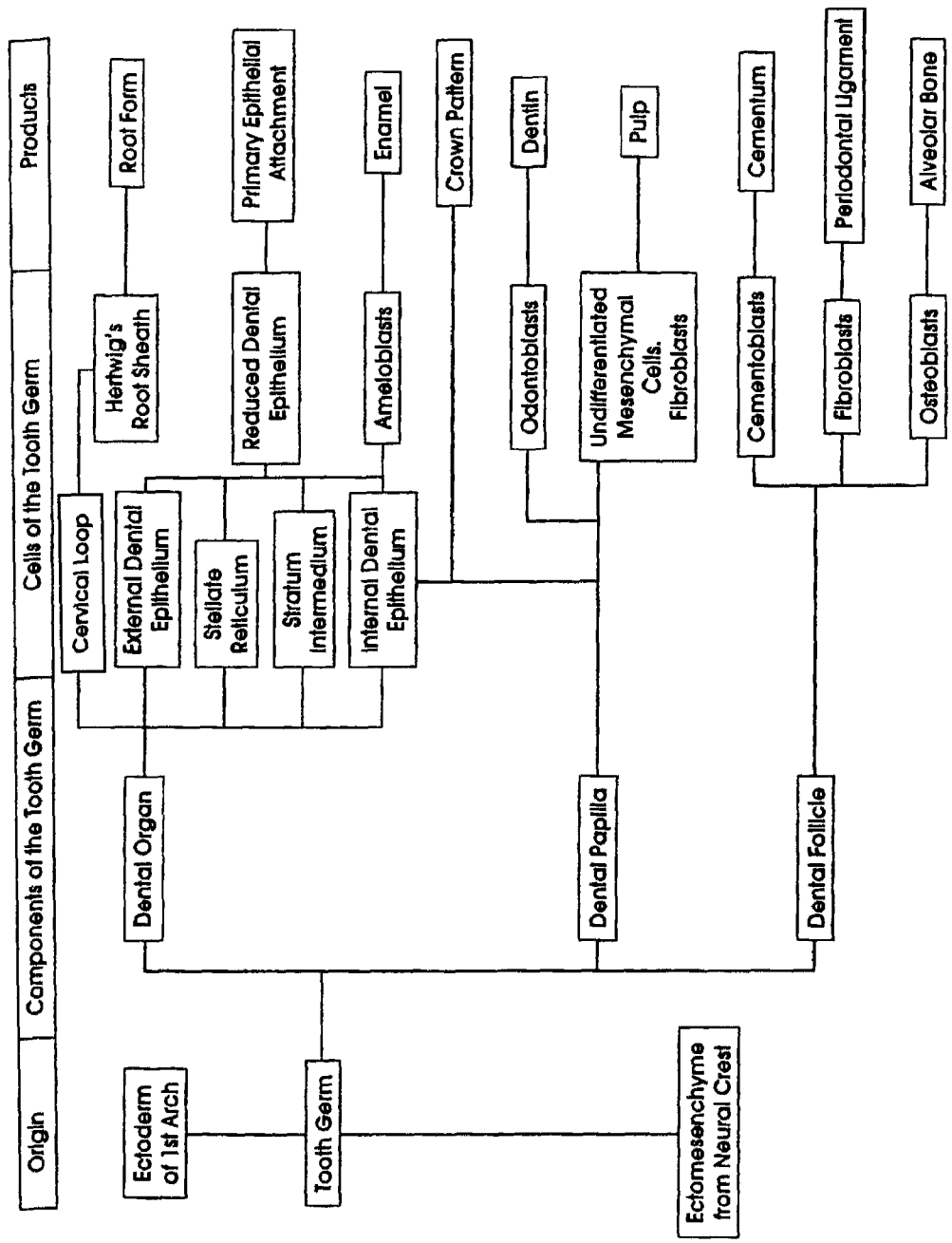

FIG. 10 diagrammatically provides a summary of the tooth development.

Figure 11:
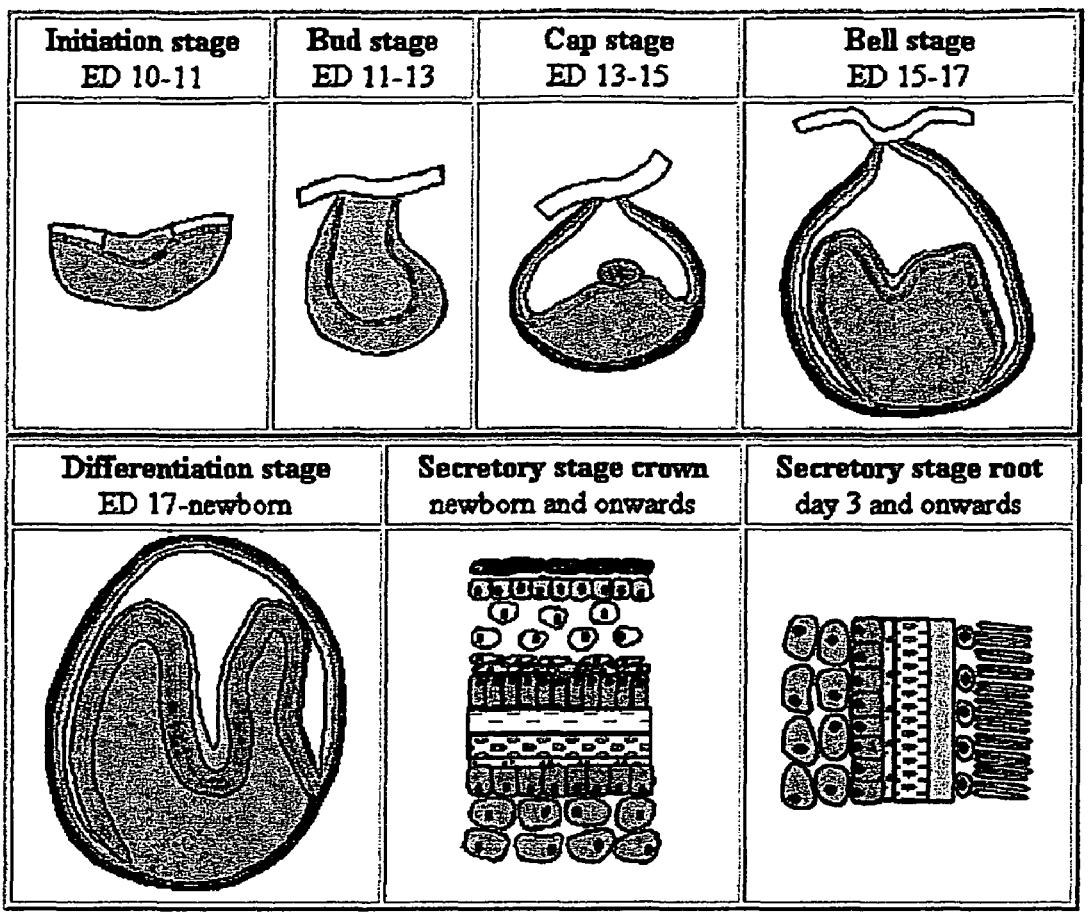

FIG. 11 pictorially depicts the development of a tooth.

DETAILED DESCRIPTION OF THE INVENTION

The stem cell of the invention is obtainable from the non-embryonic tissue isolated from the dental follicle of tooth or wisdom tooth which are able to differentiate into a periodontal ligament like membrane structure. Additionally the stem cell of the invention is able to differentiate into a mineralised tissue like structure.

The stem cell of the invention which was derived from non-embryonic or postnatal animal cells or tissue is capable of self-renewal and capable of differentiation to cells of endodermal, ectodermal and mesodermal lineages. In particular, the stem cell of the invention is a human cell.

Subject of the present invention is also a pluripotent mesenchymal stem cell obtainable from the stem cell of the invention.

The stem cell of the invention can be kept in a culture comprising:
a) pluripotent embryonic-like stem cells, derived from follicle cells capable of self-renewal and capable of differentiation to cells of mesodermal lineages; and
b) a medium capable of supporting the proliferation of said stem cells.
c) a medium capable of supporting the proliferation of said stem cells into cells building a biological membrane with blood vessel or other vascular vessels.

Preferably, this culture is further comprising a proliferation factor or lineage commitment factor. In particular the stem cells are human cells.

Subject of the invention is also a method of isolating an pluripotent embryonic-like stem cell, comprising the steps of
obtaining cells from a dental sac (dental follicle)
culturing the cells.

According to the invention a clonal pluripotent embryonic-like stem cell line can be obtained by a method of isolating, comprising the steps of
obtaining clonogenic cells from a dental follicle
culturing the cells in different media
diluting said cultured cells to clonal density;
culturing said diluted cells;
propagating those cultures having a single cell.

Thus also a clonal pluripotent embryonic-like stem cell line obtainable by this method is subject of the invention.

A stem cell of the invention which is genetically engineered to express a gene or protein of interest is also subject matter of the present invention. Such a stem cell may be generated by a method of producing a genetically engineered pluripotent embryonic-like stem cell comprising the steps of
(a) transfecting pluripotent embryonic-like stem cells with a DNA construct comprising at least one of a marker gene or a gene of interest;
(b) selecting for expression of the marker gene or gene of interest in the pluripotent embryonic-like stem cells;
(c) culturing the stem cells selected in (b).

In particular, the stem cell obtainable by this method is genetically engineered pluripotent embryonic-like stem cell, such as a dental follicle cell.

The stem cells of the invention may also be used in a method for detecting the presence or activity of an agent which is a lineage-commitment factor. This method of the invention comprises the steps of
contacting the stem cells of the invention with a sample suspected of containing an agent which is a lineage-commitment factor; and
determining the lineage of the so contacted cells by mRNA expression, Antigen expression or other means; wherein the lineage of the contacted cells indicates the presence or activity of a lineage-commitment factor in said sample.

The stem cells of the invention may also be used in a method of testing the ability of an agent, compound or factor to modulate the lineage-commitment of a lineage uncommitted cell. This method of the invention comprises
culturing the stem cells of the invention in a growth medium which maintains the stem cells as lineage uncommitted cells;
adding the agent, compound or factor under test; and
determining the lineage of the so contacted cells by mRNA expression, antigen expression or other means.

The stem cells of the invention may also be used in an assay system for screening agents, compounds or factors for the ability to modulate the lineage-commitment of a lineage uncommitted cell. This method of the invention comprises:
culturing the stem cells of the invention in a growth medium which maintains the stem cells as lineage uncommitted cells,
adding the agent, compound or factor under test; and
determining the lineage of the so contacted cells by mRNA expression, antigen expression or other means.

The stem cells of the invention may also be used in a method for detecting the presence or activity of an agent which is a proliferation factor. This method of the invention comprises the steps of
contacting the stem cells of the invention with a sample suspected of containing an agent which is a proliferation factor; and
determining the proliferation and lineage of the so contacted cells by mRNA expression, antigen expression or other means; wherein the proliferation of the contacted cells without lineage commitment indicates the presence or activity of a proliferation factor in said sample.

The stem cells of the invention may also be used in a method of testing the ability of an agent, compound or factor to modulate the proliferation of a lineage uncommitted cell. This method of the invention comprises:
culturing the stem cells of the invention in a growth medium which maintains the stem cells as lineage uncommitted cells;
adding the agent, compound or factor under test; and
determining the proliferation and lineage of the so contacted cells by mRNA expression, antigen expression or other means.

Subject matter of the present invention is also a method for culturing stem cells of the invention into membranes which will used for regenerating parodontitis, tendons, ligaments, fascia and other kinds of connecting tissues supporting differentiation to mesothelic/endothelic cells into blood vessels or ectodermal or into neuronal tissue.

According to the invention the stems cells of the invention can be cultured by a method for culturing in any media containing one or in combination for differentiation: insulin, retinoic acid, indomethacin, isobtylxanthine, theophylline, transforming-growth-factor-beta (any), bone morphogenetic protein (any), Fibroblast growth factor (any), Epidermal Growth factor (any), Platelet derived growth factor (any), Vascular endothelial growth factor (any), hepatocyte growth factor, Interferon (any), Insulin like growth factor (any), Interleukine (any), nerve growth factor.

The invention is also related to a method of ex vivo administration of a protein or gene of interest comprising the step of transfecting the pluripotent embryonic-like stem cell of the invention with a vector comprising DNA or RNA which expresses a protein or gene of interest.

Subject matter of the present invention is also a method of preventing and/or treating cellular debilitations, derangements and/or dysfunctions and/or other disease states in mammals, comprising administering to a mammal a therapeutically effective amount of pluripotent embryonic-like stem cells, or cells or tissues derived therefrom. The skilled person knows how choose time development stage of the stem cell of the invention in order to implant the stem cell as well as its dosage. For example, the cell number to be applied can vary dependent on the disease to be cured. In animal experiments typically cells were administered in a number about $10^6$ cells.

The stem cell of the invention can be used for tissue repair or transplantation in mammals by administering the stem cell to a mammal in a therapeutically effective amount of pluripotent embryonic-like stem cells, or cells or tissues derived therefrom.

According to the invention the stem cells can be used in a method of preventing and/or treating cellular debilitations, derangements 2 and/or dysfunctions and/or other disease states in mammals by administering to a mammal a therapeutically effective amount of a mesodermal lineage-committed cell derived from the stem cell of the invention.

The stem cells of the invention make possible a method of tissue repair or transplantation in mammals, comprising administering to a mammal a therapeutically effective amount of a mesodermal lineage-committed cell derived from the stem cell of the invention.

The stem cells of the invention can be essential part of a pharmaceutical composition for the treatment of cellular debilitation, derangement and/or dysfunction in mammals, comprising:
a therapeutically effective amount of pluripotent embryonic-like stem cells, or cells or tissues derived therefrom; and
a pharmaceutically acceptable medium or carrier.

In one embodiment of the pharmaceutical composition of the invention a proliferation factor or lineage-commitment factor is added.

The stem cells of the invention can be present in a scaffold, consisting of Table 1 to engineer teeth by culturing stem cells of the invention on matrices or for creating teeth-connection periodontal cell lines for treating periodontal diseases. The scaffold consisting of table 1 can also be used for building teeth-surroundings bones/bone matrix alveolar bone or jaw bone or building arterial and venous vessels in mouth.

In a further embodiment of the invention a stem cell derived from teeth is seeded on an extra cellular matrix controlling its behaviour by providing adhesion signals, and growth factor binding sites seeded on a scaffold having cell binding domain sequences according to table 2 consisting of table 1.

The invention also concerns a method of culturing of cells wherein the cells are seeded on matrices in a bioreactor.

The stem cells of the invention can be employed also in a method to implant stem cells in periodontium to rebuild periodontium, to improve healing teeth extraction and skin lesions.

Further, the stem cells of the invention are implanted in periodontium to build or repair cementum of tooth.

The invention is further described in more detail.

Detailed Description of the Invention

Culture and Isolation of Stem Cells Derived from Wisdom Teeth

In a further aspect, the present invention relates to a culture comprising:
  (a) Pluripotent embryonic-like stem cells, capable of self regeneration and capable of differentiation to cells of endodermal, ectodermal and mesodermal lineages; and
  (b) a medium capable of supporting the proliferation of said stem cells.

Such stem cell containing cultures may further comprise a proliferation factor or lineage commitment factor. The stem cells of such cultures may be isolated from non-human cells or human cells.

The invention further relates to methods of isolating an pluripotent embryonic-like stem cell. In particular, a method of isolating an pluripotent embryonic-like stem cell of the present invention, comprises the steps of
  (a) obtaining cells from a non-embryonic animal or human source-,
  (b) with or without slow freezing said cells in medium containing 7.5% (v/v) dimethyl sulfoxide until a final temperature of −80° C. is reached; and
  (c) culturing the cells.

The invention further relates to methods of isolating an pluripotent embryonic-like stem cell, In particular, a method of isolating an pluripotent embryonic-like stem cell of the present invention, comprises the steps of
  (a) obtaining cells from a postnatal animal or human source;
  (b) with or without slow freezing said cells in medium containing 7.5% (v/v) dimethyl sulfoxide until a final temperature of −80° C. is reached; and
  (c) culturing the cells.

The invention further relates to methods of isolating an pluripotent embryonic-like stem cell. In particular, a method of isolating an pluripotent embryonic-like stem cell of the present invention, comprises the steps of
  (a) obtaining cells from an adult animal or human source;
  (b) with or without slow freezing said cells in medium containing 7.5% (v/v) dimethyl sulfoxide until a final temperature of −80° C. is reached; and
  (c) culturing the cells.

The invention further relates to methods of isolating an pluripotent embryonic-like stem cell, In particular, a method of isolating an pluripotent embryonic-like stem cell of the present-invention, comprises the steps of
  (a) obtaining cells from a non-embryonic animal or human source;
  (b) filtering said cells through a strainer;
  (c) with or without slow freezing said cells in medium containing 7.5% (v/v) dimethyl sulfoxide until a final temperature of −80° C. is reached; and
  (d) culturing the cells.

In a further aspect, the methods of isolating an pluripotent embryonic-like stem cell relate to methods whereby a clonal population of such stem cells is isolated, wherein a single pluripotent embryonic-like stem cell is first isolated and then further cultured and expanded to generate a clonal population. A single pluripotent embryonic-like stem cell may be isolated by means of limiting dilution or such other methods as are known to the skilled artisan.

Genetical Engineered Stem Cells

Thus, the present invention also relates to a clonal pluripotent embryonic-like stem cell line developed by such method. In a particular aspect, the present invention relates to pluripotent embryonic-like stem cells or populations of such cells which have been transformed or transfected and thereby contain and can express a gene or protein of interest. Thus, this invention includes pluripotent embryonic-like stem cells genetically engineered to express a gene or protein of interest. In as much as such genetically engineered stem cells can then undergo lineage-commitment, the present invention further encompasses lineage-committed cells, which are derived from a genetically engineered pluripotent embryonic-like stem cell, and which express a gene or protein of interest.

The lineage-committed cells may be endodermal, ectodermal or mesodermal lineage-committed cells and may be pluripotent, such as a pluripotent mesenchymal stem cell, or progenitor cells, such as an adipogenic or a myogenic cell. The invention then relates to methods of producing a genetically engineered pluripotent embryonic-like stem cell comprising the steps of
  (a) transfecting pluripotent embryonic-like stem cells with a DNA construct comprising at least one of a marker gene or a gene of interest;
  (b) selecting for expression of the marker gene or gene of interest in the pluripotent embryonic-like stem cells;
  (c) culturing the stem cells selected in (b).

In a particular aspect, the present invention encompasses genetically engineered pluripotent embryonic-like stem cell(s), including human and non-human cells, produced by such method. The present invention further relates to methods for detecting the presence or activity of an agent which is a lineage-commitment factor comprising the steps of
  A. contacting the pluripotent embryonic-like stem cells of the present invention with a sample suspected of containing an agent which is a lineage-commitment factor; and
  B.—determining the lineage of the so contacted cells by morphology, mRNA expression, antigen expression or other means;
wherein the lineage of the contacted cells indicates the presence or activity of a lineage-commitment factor in said sample.

Assays for Cell Modulating Agents

The present invention also relates to methods of testing the ability of an agent, compound or factor to modulate the lineage-commitment of a lineage uncommitted cell which comprises A. culturing the pluripotent embryonic-like stem cells of the present invention in a growth medium which maintains the stem cells as lineage uncommitted cells; and
B. adding the agent, compound or factor under test
C. determining the lineage of the so contacted cells by morphology, mRNA expression, antigen expression or other means.

The invention includes an assay system for screening of potential agents, compounds or drugs effective to modulate the proliferation or lineage-commitment of the pluripotent embryonic-like stem cells of the present invention.

In a further such aspect, the present invention relates to an assay system for screening agents, compounds or factors for the ability to modulate the lineage-commitment of a lineage uncommitted cell, comprising:
A. culturing the pluripotent embryonic-like stem cells of the present-invention in a growth medium which maintains the stem cells as lineage uncommitted cells
B. adding the agent, compound or factor under test; and
C. determining the lineage of the so contacted cells by morphology, mRNA expression, antigen expression or other means.

The invention also relates to a method for detecting the presence or activity of an agent which is a proliferation factor comprising the steps of.
A. contacting the pluripotent embryonic- like stem cells of the present invention with a sample suspected of containing an agent which is a proliferation factor; and
B. determining the proliferation and lineage of the so contacted cells by morphology, mRNA expression, antigen expression or other means; wherein the proliferation of the contacted cells without lineage commitment indicates the presence or activity of a proliferation factor in said sample.

In a further aspect, the invention includes methods of testing the ability of an agent, compound or factor to modulate the proliferation of a lineage uncommitted cell which comprises
B. culturing the pluripotent embryonic-like stem cells of the present invention in a growth medium which maintains the stem cells as lineage uncommitted cells;
C. adding the agent, compound or factor under test; and
D. determining the proliferation and lineage of the so contacted cells by mRNA expression, antigen expression or other means.

The invention further relates to an assay system for screening agents, compounds or factors for the ability to modulate the proliferation of a lineage uncommitted cell, comprising:
A. culturing the pluripotent embryonic-like stem cells of the present invention in a growth medium which maintains the stem cells. as lineage uncommitted cells;
B. adding the agent, compound or factor under test; and
C. determining the proliferation and lineage of the so contacted cells by mRNA expression, antigen expression or other means.

The assay system could importantly be adapted to identify drugs or other entities that are capable of modulating the pluripotent embryonic-like stem cells of the present invention, either in vitro or in vivo. Such an assay would be useful in the development of agents, factors or drugs that would be specific in modulating the pluripotent embryonic-like stem cells to, for instance, proliferate or to commit to a particular lineage or cell type. For example, such drugs might be used to facilitate cellular or tissue transplantation therapy.

The assay system(s) could readily be adapted to screen, identify or characterize genes encoding proliferation or lineage-commitment factors or encoding proteins or molecules otherwise involved in cellular differentiation and development.

For instance, genes encoding proteins involved in or expressed during differentiation along a particular lineage could be identified by known methods (for instance cDNA libraries, differential display, etc. Thus, the pluripotent embryonic-like stem cells of the present invention could be cultured under conditions giving rise to a particular lineage and the genes therein expressed then characterized. Factors and proteins necessary for maintaining the pluripotent embryonic-like stem cells of the present invention in a pluripotent embryonic-like state might also be similarly identified and characterized by culturing the pluripotent embryonic-like stem cells of the present invention under conditions maintaining their self-renewal capacity and characterizing the genes and proteins so expressed or which, when provided exogenously, will maintain the self-renewal capacity.

Transplantation

In a further embodiment, the present invention relates to certain therapeutic methods which would be based upon the activity of the pluripotent embryonic-like stem cells of the present invention, including cells or tissues derived therefrom, or upon, agents or other drugs determined to act on any such cells or tissues, including proliferation factors and lineage-commitment factors. One exemplary therapeutic method is associated with the prevention or modulation of the manifestations of conditions causally related to or following from the lack or insufficiency of cells of a particular lineage, and comprises administering the pluripotent embryonic-like stem cells of the present invention, including cells or tissues derived therefrom, either individually or in mixture with proliferation factors or lineage-commitment factors in an amount effective to prevent the development or progression of those conditions in the host.

In a further and particular aspect the present invention includes therapeutic methods, including transplantation of the pluripotent embryonic-like stem cells of the present invention, including lineage-uncommitted populations of cells, lineage-committed populations of cells, tissues and organs derived there from, in treatment or alleviation of conditions, diseases, disorders, cellular debilitations or deficiencies which would benefit from such therapy. These methods include the replacement or replenishment of cells, tissues or organs. Such replacement or replenishment may be accomplished by transplantation of the pluripotent embryonic-like stem cells of the present invention or by transplantation of lineage-uncommitted populations of cells, lineage-committed populations of cells, tissues or organs derived therefrom.

Thus, the present invention includes a method of transplanting pluripotent embryonic-like stem cells in a host comprising the step of introducing into the host the pluripotent embryonic-like stem cells of the present invention.

In a further aspect this invention provides a method of providing a host with purified pluripotent embryonic-like stem cells comprising the step of introducing into the host the pluripotent embryonic-like stem cells of the present invention.

In a still further aspect, this invention includes a method of in vivo administration of a protein or gene of interest comprising the step of transfecting the pluripotent embryonic-like stem cells of the present invention with a vector comprising DNA or RNA which expresses a protein or gene of interest.

The present invention provides a method of tissue repair or transplantation in mammals, comprising administering to a mammal a therapeutically effective amount of pluripotent embryonic-like stem cells.

The present invention provides a method of preventing and/or treating cellular debilitations, derangements and/or dysfunctions and/or other disease states in mammals, comprising administering to a mammal a therapeutically effective amount of pluripotent embryonic-like stem cells.

In a further aspect, the present invention provides a method of preventing and/or treating cellular debilitations, derangements and/or dysfunctions and/or other disease states in mammals, comprising administering to a mammal a therapeutically effective amount of a endodermal, ectodermal or mesodermal lineage-committed cell derived from the pluripotent embryonic-like stem cells of the present invention.

The therapeutic method generally referred to herein could include the method for the treatment of various pathologies or other cellular dysfunctions and derangements by the administration of pharmaceutical compositions that may comprise proliferation factors or lineage-commitment factors, alone or in combination with the pluripotent embryonic-like stem cells of the present invention, or cells or tissues derived therefrom, or other similarly effective agents, drugs or compounds identified for instance by a drug screening assay prepared and used in accordance with a further aspect of the present invention.

Pharmaceutical Compositions

It is a still further object of the present invention to provide pharmaceutical compositions for use in therapeutic methods which comprise or are based upon the pluripotent embryonic-like stem cells of the present invention, including lineage-uncommitted populations of cells, lineage-committed populations of cells, tissues and organs derived therefrom, along with a pharmaceutically acceptable carrier. Also contemplated are pharmaceutical compositions comprising proliferation factors or lineage commitment factors that act on or modulate the pluripotent embryonic-like stem cells of the present invention and/or the cells, tissues and organs derived therefrom, along with a pharmaceutically acceptable carrier. The pharmaceutical compositions of proliferation factors or lineage commitment factors may be further comprise the pluripotent embryonic-like stem cells of the present invention, or cells, tissues or organs derived therefrom. The pharmaceutical compositions may comprise the pluripotent embryonic-like stem cells of the present invention, or cells, tissues or organs derived therefrom, in apolymeric carrier or extracellular matrix.

This invention also provides pharmaceutical compositions for the treatment of cellular debilitation, derangement and/or dysfunction in mammals, comprising:

A. a therapeutically effective amount of the pluripotent embryonic-like stem cells of the present invention; and C. a pharmaceutically acceptable medium or carrier.

Pharmaceutical compositions of the present invention also include compositions comprising endodermal, ectodermal or mesodermal lineage-committed cell(s) derived from the pluripotent embryonic-like stem cells of the present invention, and a pharmaceutically acceptable medium or carrier. Any such pharmaceutical compositions may further comprise a proliferation factor or lineage- commitment factor.

Development of Teeth

In the following diagram a summary of the tooth development is shown. The origin of the tooth is the tooth germ with the ability to form all cells building a tooth. Here one has a stage of pluripotency, a undifferentiated precursor stage, with the capability to differentiate to cells of the dental organ, dental papilla and dental follicle.

This is shown in FIG. 10. Citation from: A. R. Ten Cate, Oral Histology, Fifth Ed., Mosby Inc. 1998

Initiation of the Tooth

FIG. 11 explains the development of a tooth.

First arch epithelium loses this odontogenic potential, which is then assumed by the ectomesenchyme so that it can elicit tooth formation from a variety of epithelia. For example, recombination of late first arch ectomesenchyme with embryonic plantar (foot) epithelium changes the development direction of the epithelium so that a dental organ is formed Conversely, if the epithelial dental organ is recombined with skin mesenchyme, it loses its dental characteristics and assumes those of epidermis. What these experiments show is that odontogenesis is first initiated by factors resident in the first arch epithelium influencing ectomesenchyme. These experimental findings are mirrored by the expression pattern of transcription and growth factors in these tissues. Thus bone morphogenetic protein (BMP) 2 and 4 are specially and transiently expressed in the epithelium at sites where the teeth will form, and it has been shown experimentally that they upregulate the expression of several molecules, especially BMP4 and the homeobox genes MSX1 and MSX2 in the ectomesenchyme. Thus the evidence from experimental embryology, recombinant DNA technology, and immunocytochemistry indicates that first arch epithelium is essential for the initiation of tooth development. Once the ability to initiate tooth development has been acquired by ectomesenchyme, it is maintained by dental papillary cells. Thus, if early tooth germs are cultured for an extended period, the cells dedifferentiated and the morphology of the germs is completely lost; yet, if these dedifferentiated epithelial and ectomesenchymal cells are harvested and recombined in vivo, they form a tooth (the program for tooth formation is not lost). Of particular interest in this regard is the finding that, if mouse tooth ectomesenchyme is combined with chick epithelium, teeth develop.

Bell Stage (Histodifferentiation and Morphodifferentiation)

At the periphery of the dental organ, the cells assume a cuboidal shape and form the external, or outer, dental epithelium. The cells bordering on the dental papilla differentiate into two histologically distinct components. Those immediately adjacent to the dental papilla assume a short columnar shape and are characterized by high glycogen content; together they form the internal (or inner) dental epithelium. Between the internal dental epithelium and the newly differentiated stellate reticulum some epithelial cells differentiate into a layer called the stratum intermedium. The cells of this layer are soon characterized by an exceptionally high activity of the enzyme alkaline phosphatase. Although the cells of this layer are histologically distinct from the cells of the internal dental epithelium, both layers should be considered as a single function unit responsible for the formation of enamel. The internal dental epithelium meets the external dental epithelium at the rim of the dental organ; this junctional zone is known as the cervical loop.

Clusters of blood vessels are found ramifying around the tooth germ in the dental follicle and entering the dental papilla (or pulp) during the cap stage. During tooth eruption the dental follicle build periodontal ligament, alveolar bone and cementum. The Periodontal ligament (PDL) is a connective tissue with fibroblasts, collagen and vascular channels and blood vessels which defined a membrane like structure.

EXAMPLES

Subjects and Cell Culture. Normal human impacted third molars were collected from adults (various age). Dental follicle surfaces were cleaned and minced by using sterilized scalpel. The tissue was digested in a solution of 0.1 U/ml collagenase type 1 and 1 U/ml dispase (Roche Mannheim) for 1 h at 37° C. Moreover also cells were isolated from dental follicle tissue after mincing and washing with a balanced salt solution with trypsin. For this purpose, tissue pieces were incubated in a 0.250% trypsin in D-MEM without Calcium supplemented with EDTA for up to 18 h for a maximal penetration with little trypsin activity. Trypsin were decant and discard and tissue were treated with residual trypsin at 37° C. for 20 min-30 min in phosphate buffer. Single-cell suspensions were obtained by passing the cells through a 70-µm strainer (Falcon). Bone marrow cells, processed from marrow aspirates of normal human adult volunteers were purchased from Poietic Technologies and then washed in growth medium. Single-cell suspensions or minced and digested tissue of dental follicle were seeded into 60 mm plates with different medias: Knockout D-MEM serumreplacement media (GIBCO/BRL) supplemented with 2 mM L-glutamine/100 units/ml. penicillin/100 µg/ml streptomycin (Biofluids, Rockville, Md.) or DMEM (Biochrom) supplemented with 200% FCS (Equitech-Bio, Kerrville, Tex.)/100 µM L-ascorbic acid 2-phosphate (Wako Pure Chemicals, Osaka)/2 mM L-glutamine/100 units/ml penicillin/100 µg/ml streptomycin (Biofluids, Rockville, Md.) or MSCBM Bullet-Kit (Poietics) and then incubated at 37° C. in 5% $CO_2$. Bone marrow cells were cultured in MSCBM BulletKit (Poietics). To assess colony-forming efficiency, day 14 cultures were fixed with 4% formalin, and then stained with 0.1% toluidine blue. For the induction of calcified bone matrix deposition in vitro cells were cultured in D-MEM (Biochrom) supplemented with 10% FCS, 2 mM L-Glutamine (sigma), $10^{-8}$ M Dexamethason (sigma), 100 µM L-ascorbic acid 2-phosphate, 1.8 mM $KH_2PO_4$ (Sigma), 20 mM HEPES (Sigma). The proliferation rate of subconfluent cultures of Dental follicle Stem cells (DFSCs) and Bone marrow stromal cells (BMSCS) was assessed by bromodeoxyuridine (BrdUrd) incorporation for 24 h by using a Zymed BrdUrd staining kit (Vector Laboratories).

Immunohistochemistry. Dental follicle were fixed in 4% formalin and embedded in paraffin. Slices were subjected for immunohistochemistry. Primary DPSCs and BMSCs were subcultured. The cells were fixed in 4% formalin. Slices and cells were reacted with saturating levels of primary antibodies and the corresponding control antibodies by using a Zymed broad-spectrum immunoperoxidase kit (Vector Laboratories). Working dilutions of serum, monoclonal supernatants, and purified antibodies were used. Antibodies used: Notch Ab-1 (A6) Mouse Mab (anti-Notch1) (NeoMarkers), AC 133/2 (anti-CD133) (Miltenyi), Flk-1 (anti-VEGFR-2), Mouse IgG1 (clone 53) anti mouse FNK (fibroblast growth factor), Mouse IgG1 (clone 25) anti rat Nestin, Mouse IgG1 (clone 52 anti human GFAP (glial fibrillary acidic protein) (BD Bioscience).

Histochemistry. Secondary DFSC and BMSC cultures were washed in PBS and then fixed with 4% formalin. Calcium deposits were detected by treatment with 2% Alizarin Red S (pH 4.2). Staining of tissues were done with trichrom and Haematoxylin/Eosin staining procedures.

Reverse Transcription-PCR. Total RNA was prepared isolated cells by using Rneasy® Kit (Qiagen®, Hilden). First-strand cDNA synthesis was performed by using 0.1 µg-1 µg Total RNA and the Omniscript Kit (Qiagen®, Hilden) by using an oligo-dT primer (invitrogen). The qiagen HotStar-Taq Master Mix (Qiagen®, Hilden) were used for PCR. For qPCR the Quantitect® Sybr Green Kit (Qiagen®) were used. The standard program for all PCRs was 95° C. for 15 min (for enzyme activation) and 35 cycles with 95° C. for 45 sec, 55° C. for 30 sec and 72° C. for 1 min and a final extension by 72° C. for 5 min. (for primers table A). For standard PCR a PCRexpress thermocycler (thermohybaid) was used and for qPCR (quantitative PCR) an Opticon (MJ Research) with Opticon Monitor software was used. For quantification of PCR products the delta/delta calculation was used described by Winer et al. 1999 with Excel software package. The GAPDH gene was used for reference gene in all applications.

TABLE A

| Primers for PCR | | |
|---|---|---|
| Gene | Forward 5' => 3' | Reverse 5' => 3' |
| GAPDH (Glyceraldehyde-3-phosphat-dehydrogenase) | CGTCTTCACCACCATGGAGA (SEQ ID NO: 1) | CGGCCATCACGCCACAGTTT (SEQ ID NO: 2) |
| Col_1 (collagen type1) | AGGCCCTCAAGGTTTCCAAGG (SEQ ID NO: 3) | CCAGACCATVGTGTCCCCTAA (SEQ ID NO: 4) |
| Col_3 (collagen type3) | TGGTGTTGGAGCCGCTGCCA (SEQ ID NO: 5) | CTCAGCACTAGAATCTGTCC (SEQ ID NO: 6) |
| Col_12 (collagen type12) | GGAGACAGAGGCTTCACTGG (SEQ ID NO: 7) | ACTGCTCGCATCATGTTCTG (SEQ ID NO: 8) |
| Col_18 (collagen type18) | GTGCAGTATCATGCCCTGTG (SEQ ID NO: 9) | AACAGGTCTGGGTTTTGTGC (SEQ ID NO: 10) |
| Neurofilament | ACCCGACTCAGTTTCACCAG (SEQ ID NO: 11) | TCAGCCTTAGACGCCTCAATAG (SEQ ID NO: 12) |
| Nestin | GCCCTGACCACTCCAGTTTA (SEQ ID NO: 13) | GGAGTCCTGGATTTCCTTCCTA (SEQ ID NO: 14) |

TABLE A-continued

| Primers for PCR | | |
|---|---|---|
| Gene | Forward 5' => 3' | Reverse 5' => 3' |
| CD133 | CAGTCTGACCAGCGTGAA AA (SEQ ID NO: 15) | GGCCATCCAAATCTGTCCTA (SEQ ID NO: 16) |
| CD34 | TGAAGCCTAGCCTGTCAC CT (SEQ ID NO: 17) | CGCACAGCTGGAGGTCTTAT (SEQ ID NO: 18) |
| VEGFR-2 | GGTATTGGCAGTTGGAGG AA (SEQ ID NO: 19) | ACATTTGCCGCTTGGATAAC (SEQ ID NO: 20) |
| Vimentin | GGGACCTCTACGAGGAGG AG (SEQ ID NO: 21) | CGCATTGTCAACATCCTGTC (SEQ ID NO: 22) |
| FGFR1-IIIC (FGFR = Fibroblast-Growth-Factor-Receptor) | GGCAAGGAATTCAAACCT GAC (SEQ ID NO: 22) | CATCACGGCTGGTCTCTCT TC (SEQ ID NO: 23) |
| FGFR2-IIIB | AACGGGAAGGAGTTTAAG GAG (SEQ ID NO: 24) | GGAGCTATTTATCCCCGAG TG (SEQ ID NO: 25) |
| FGFR2-IIIC | TGGCAGAACTGTCAACCA TGC (SEQ ID NO: 26) | AACGGGAAGGAGTTTAAG CAG (SEQ ID NO: 27) |
| FGFR3-IIIB | AACGGCAGGGAGTTCCGC GGC (SEQ ID NO: 28) | CTTGGGGCCCGTGAACAC GCAGCC (SEQ ID NO: 29) |
| FGFR3-IIIC | AACGGCAGGGAGTTCCGC GGC (SEQ ID NO: 30) | GCAGCACCAGCCACGCAG AGT (SEQ ID NO: 31) |
| FGFR4 | GATGGACAGGCCTTTCAT GGG (SEQ ID NO: 32) | TGCTGCGGTCCATGTGGG GTCCTC (SEQ ID NO: 33) |
| IGFB-7 (Insulin-like-binding protein 7) | TGATATGCATGCTTTTCT TCTG (SEQ ID NO: 34) | TGGTTGATGCCCTTACATGA (SEQ ID NO: 35) |
| PHEX | AAAAGGCGAGAGCTGTTT TGGC (SEQ ID NO: 36) | TAAACCAGCGTCCCAGCTA CCA (SEQ ID NO: 37) |
| BS (Bonesialoprotein) | CTATGGAGAGGACGCCAC GCCTGG (SEQ ID NO: 39) | CATAGCCATCGTAGCCTTG TCCT (SEQ ID NO: 38) |
| OCN (Osteocalcin) | CATGAGAGCCCTCACA (SEQ ID NO: 41) | AGAGCGACACCCTAGAC (SEQ ID NO: 42) |
| FGF-7 (Fibroblast-Growth-Factor 7) | ATACTGACATGGATCCTG CCA (SEQ ID NO: 43) | TCCAACTGCCACGGTCCTG AT (SEQ ID NO: 44) |
| IGF-2 (Insulin-like-Growth-Factor 2) | CTCTCCGTGCTGTTCTCT CC (SEQ ID NO: 45) | CGGGCCAGATGTTGTACTTT (SEQ ID NO: 46) |
| AP (Alkaline-Phosphatase) | TGGAGCTTCAGAAGCTCA ACACCA (SEQ ID NO: 47) | ATCTCGTTGTCTGAGTACC AGTCC (SEQ ID NO: 48) |
| DSPP | CCTAAAGAAAATGAAGAT AATT (SEQ ID NO: 49) | TAGAAAAACTCTTCCCTCC TAC (SEQ ID NO: 50) |

Isolation of DFSC. Notch-1 and Nestin positive cells were identified by immune-histochemistry in dental follicle slices (FIG. 1. α and β), which were described as markers of putative stem cells in dental epithelium and neural stem cells (Harada et al. 1999, Johansson et al. 1999b), but were negative for CD133, VEGFR-2 and GFAP (table B).

FIG. 1 shows immunephenotype of dental follicle. Studies based on immunoperoxidase reactivity were performed with slices of dental follicle. Antibodies: α) Notch-,1β) Nestin.

Friedenstein et al. 1976 documented that osteoprogenitors can be isolated from aspirates of bone marrow by their ability to adhere to a plastic substratum or colony forming unit fibroblast (CFU-F). The presence of a clonogenic and plastic adherent cell population in dental follicle tissue (FIG. 2 α). is demonstrated. The cells within each colony were characterized by a typical fibroblast-like morphology analogous to the progeny of human bone marrow CFU-F and they were positive for Notch-1 and Nestin by immunochemistry (FIG. 2 β and γ).

FIG. 2 shows a) Representative colony after 14 days. β) and γ) characterize immunophenotypes of cultured DFSC with representative staining pattern for β) Nestin and γ) Notch-1.

Immunohistochemical studies were performed to characterize DFSC from dental follicle, by using antibodies specific to known antigens associated with different phenotypes. Representative immunoreactivity patterns for DPSC are shown (Table B).

TABLE B

Summary of immunophenotypes of dental follicle and cultured DFSCs. Tissue/Cells

| Antibody | Dental-Follicle | DFSC A | DFSC B | BMSC A |
|---|---|---|---|---|
| Nestin | + | + | + | + |
| Notch-1 | ++ | + | ++ | + |
| AC133 | − | ND | ND | ND |
| VEGFR-2 | − | ND | ND | ND |
| GFAP | − | ND | ND | ND |

+ = positive
++ = strong positive
− = negative
A: DFSC in MSCBM BulletKit;
B: DFSC in: Knockout D-MEM serum replacement media,
ND: not determined The frequencies of colony-forming cells derived from dental follicle tissue were in MSCBM BulletKit: $30/10^4$ cells plated and in supplemented DMEM media: $15/10^4$ cells plated. In contrast no colonies were yielded in Knockout D-MEM serumreplacement media after 14 days. But cells were cultured in spheroid shaped morphology over a longer period. The average number of proliferating cells in DPSC cultures of two different donors was higher (9.7% BrdUrd positive cells +−1.5 SEM) when compared with BMSC cultures (6.40% BrdUrd-positive cells +−0.80% SEM by using the BrdUrd uptake method.

Characterization of the Phenotype of DFSCs In Vitro by RT-PCR and RT-QPCR.

Many of the markers in Table C were expressed, in the DFSC population and in the BMSC population. The DFSC cells were found to be negative for the odontoblast-specific marker, DSPP. We have also found no gene expression determined for mRNAs of BMSC and DFSC of neurofilament, VEGFR-2, FGFR2-IIIB and FGFR3-IIIB (Table C).

TABLE C

RT-PCR with BMSC and DFSC grown in MSCBM BulletKit.

| Gene | BMSC | DFSC |
|---|---|---|
| GAPDH (Glyceraldehyde-3-phosphat-dehydrogenase) | + | + |
| Col_1 | + | + |
| Col_3 | + | + |
| Col_12 | + | + |
| Col_18 | + | + |
| Neurofilament | − | − |
| Nestin | + | + |
| CD133 | − | − |
| CD34 | − | − |
| VEGFR-2 | − | − |
| Vimentin | + | + |
| FGFR1-IIIC (FGFR = Fibroblast-Growth-Factor-Receptor) | + | + |
| FGFR2-IIIB | − | − |
| FGFR2-IIIC | + | + |
| FGFR3-IIIB | − | − |
| FGFR3-IIIC | + | (+) |
| FGFR4 | + | + |
| PHEX | + | + |
| BS (Bonesialoprotein) | + | + |
| OCN (Osteocalcin) | + | + |
| FGF-7 (Fibroblast-Growth-Factor 7) | + | + |
| IGF-2 (Insulin-like-Growth-Factor 2) | (+) | + |
| AP (Alkaline-Phosphatase) | + | + |
| DSPP | − | − |

+ = positive;
− = negative;
(+) = faint positive;
ND = not determined

DPSC and BMSC express collagen1, bonesialoprotein, osteocalcin and phex. These genes are typically for osteoprogenitor cells. Both cell types express FGFR1-IIIC, which were detected also by fibroblast isolated from the periodontal ligament, but not CD34 and CD133, common marker for haematopoietic stem cells. We detected faint differences for IGF-2 and FGFR3-IIIC for gene expression. Interestingly The intensity of the IGF-2 signal was better for DFSC than for BMSC. Because of the missing differences DFSC and BMSC were investigated with qPCR (FIG. C). It was detected that IGF-2 expression in DFSC cells was more than 100 time increased compared to the BMSC cells, in contrast the expression of BS and OCN was decreased (15 times).

Interestingly stem cells have different expression patterns for collagens cultured in knock-out D-MEM or in MSCBM BulletKit. Gene expressions for Col_1 and Col_3 were 126 times and 82 times respectively increased for DFSCs cultured in knockout D-MEM serumreplacement in comparison to DFSCs cultured in media derived from the MSCBM Bullet-Kit (FIG. 3b). Knockout D-MEM cultivated cells with high collagen expression and a spheroid-like structure are comparable in shape and gene-expression with recently published cultivated dental follicle cells derived from bovine. Handa et al. 2002 described follicle cells as cementoblast progenitor cells which were unable to differentiate into mineralised cells in vitro, but in vivo (Handa K. et al. (2002) bone 31(5): 606-611). DFSCs maturated probably in knock-out D-MEM serumreplacement media to spheroid-like structures.

FIG. 3a shows QPCR with cultured BMSC and DFSC grown in MSCBM BulletKit. Values for relative concentration were calculated with delta/delta method (Winer et al. 1999), total RNA from BMSCs were used as calibrator. House-keeping gene was GAPDH.

FIG. 3b shows QPCR with cultured DFSC grown in MSCBM BulletKit, D-MEM supplemented with 20% FCS and knockout D-MEM (serumreplacement). Values were calibrated with total RNA derived from DFSC cultured in MSCBM Bulletkit.

Dexamethasone Analysis for Phenotypic Expression

Clones were examined using insulin and dexamethasone to determine their identity, i.e., either lineage-committed progenitor cells or lineage-uncommitted pluripotent cells. Lineage-induction agents, such as dexamethasone, induce lineage-commitment and expression in pluripotent cells, but does not alter phenotypic expression in progenitor cells. Cultures treated with dexamethasone will exhibit multiple expressed phenotypes. Thus comparing the effects of treatment with dexamethasone and insulin can identify specific types of progenitor and pluripotent cells within an unknown group of cells Differentiation Potential of DFSCs and BMSCs in vitro. Long-term cultures (5-6 weeks) of DFSCs grown in the presence of L-ascorbate-2-phosphate, the glucocorticoid, dexamethasone, and inorganic phosphate demonstrated the capacity to form Alizarin Red-positive fields with high levels of calcium (FIG. 4). The deposits were scattered throughout as single mineralized zones or over the entire adherent layer. In contrast, BMSC culture produced extensive sheets of calcified deposits over the entire adherent layer after 6 weeks of induction (FIG. 4).

FIG. 4 shows the differentiation of DFSC and BMSC in vitro: Adherent layers of cultured DFSCs (α, β) and BMSC (γ), are shown with Alizarin Red staining as a measure of calcium accumulation following 5 (β) and 6 weeks (α, γ) of induction with DMEM with 100% FCS, L-acorbate-2-phosphate, inorganic phosphate and dexamethasone.

After 5 weeks of stimulation with dexamethasone, a layer built from long-term cultures of DFSCs, a novel Follicle-tissue-membrane (FTM). The membrane was transparent, substantial and flexible and—as shown in FIG. 5—lost partial tight contacts to the base of the culture bottle. This phenomena was not found for BMSCs.

FIG. 5 shows differentiation of DFSC to a novel follicle-tissue-membrane (FTM) in vitro: Culture bottle with layer of cultured DFSCs are shown with Alizarin Red staining as a measure of calcium accumulation following 5 weeks of induction with DMEM with 10% FCS, L-acorbate-2-phosphate, inorganic phosphate and dexamethasone.

The differentiated cells for Notch-1 and Nestin were tested. Interestingly only differentiated cells yielded from BMSCs expressed Notch-1 and Nestin, whereas only Nestin was detected for the progenies of DFSC grown in media with dexamthesone (table D).

TABLE D

Immunohistochemical analysis of long term cultures of DFSC and BMSC (6 weeks) incubated with dexamethason (diff) and without (undiff)

| Cells | Notch-1 | Nestin |
| --- | --- | --- |
| DFSC diff | − | + |
| DFSC undiff | + | + |
| BMSC diff | + | + |
| BMSC undiff | + | +? |

Moreover the gene expression of long term cultures of BMSC and DFSC incubated with and without dexamethason with QPCR (FIG. 6) were investigated.

FIG. 6 shows QPCR with cDNA from DFSCs cultured in media with and without dexamethason: For abbreviation see above.

Differentiated cells expressed more collagen type 18, collagen type 3, PHEX, Osteocalcin and PHEX than DFSC untreated with dexamethason. Surprisingly it was found only equal expression rates for bonesialoprotein, collagen type 1 and alkaline phosphatase, which are typically increased by cells responsible for bone formation. One can conclude, that the progeny of DFSC incubated in dexamethason build a special kind of connective tissue (FTM). FTM was isolated and thin slices were made for histochemical analysis. In HE- and trichrom-staining connective tissue like structure was found with parallel collagen filaments and fibroblastic/fibrocystic like cells. The collagenic structure was supported by green filaments after trichrom-staining. Thin cell layers with compacted mesothelic or endothelic cells were approximately to the connective tissue (FIG. 7). At least thin vascular vessels has built inside the connective tissue matrix of FTM. In conclusion, all these facts confirm the biological membrane structure of FTM.

FIG. 7 shows HE- and Trichrom-Stainings with FTM-Slices.

Tissue Engineering for Periodontal Applications with Stem Cells from Teeth

Tissue Engineering of Teeth and Surrounding Tissue

Use of Biodegradable Polymers as scaffolds for engineering of teeth, and teeth related tissues such as nerves, bones and connecting tissue (periodontium)

The pharmaceutical compositions of the present invention may comprise the pluripotent embryonic-like stem cells of the present invention, or cells, tissues or organs derived there from, alone or in a polymeric carrier or extracellular matrix. Suitable polymeric carriers include porous meshes or sponges formed of synthetic or natural polymers, as well as polymer solutions. One form of matrix is a polymeric mesh or sponge; the other is a polymeric hydrogel. Natural polymers that can be used include proteins such as collagen, albumin, and fibrin; and polysaccharides such as alginate and polymers of hyaluronic acid. Synthetic polymers include both biodegradable and non-biodegradable polymers.

Biodegradable Polymer Selection Criteria

Biodegradable polymers are applicable to those tissue engineering products for which tissue repair or remodelling is the goal, but not where long-term materials stability is required. Biodegradable polymers must also possess (1) manufacturing feasibility, including sufficient commercial quantities of the bulk polymer; (2) the capability to form the polymer into the final product design;
(3) mechanical properties that adequately address short-term function and do not interfere with long-term function;
(4) low or negligible toxicity of degradation products, in terms of both local tissue response and systemic response; and
(5) drug delivery compatibility in applications that call for release or attachment of active compounds.

Examples of biodegradable polymers include polymers of hydroxy acids such as polylactic acid (PLA), polglycolic acid (PGA), and polylactic acid-glycolic acid (PLGA), polyorthoesters, polyanhydrides, polyphosphazenes, and combinations thereof.

Biologically Derived Bioresorbables

Collagen is one of the most important scoffold for tissue engineering.

Glycosaminoglycans

Glycosaminoglycans (GAGs), which consist of repeating disaccharide units in linear arrangement, usually include an uronic acid component (such as glucuronic acid) and a hexosamine component (such as n-acetyl-d-glucosamine). The predominant types of GAGs attached to naturally occurring core proteins of proeoglycans include chondroitin sulfate, dermatan sulfate, keratan sulfate, and heparan sulfate. The GAGs are attached to the core protein by specific carbohydrate sequences containing three or four monosaccharides.

The largest GAG, hyaluronic acid (Hyaluronan), is an anionic polysaccharide with repeating disaccharide units of n-acetylglucosamine and glucoronic acid, with unbrached units ranging from 500 to several thousand. Hyaluronic acid can be isolated from natural sources (e.g., rooster combs) or via microbial fermentation. Because of its water-binding capacity, dilute solutions of hyaluronic acid are viscous.

Like collagen, hyaluronic acid can easily chemically modified, as by etherification of the carboxyl moieties, which reduces its water solubility and increases its viscosity (Hyaluronic acid can be cross-linked to form molecular weight complexes in the range 8 to $24 \times 10^6$ or to form an infinite molecular network (gels). In one method, hyaluronic acid is cross-linked using aldehydes and small proteins to form bonds between the C—OH groups of the polysaccharide and the amino to imino groups of the protein, thus yielding high-molecular-weight complexes. The resultant infinite-network gels can be formed into sheaths, membranes, tubes, sleeves, and particles of various shapes and sizes.

Polyhydroxyalkanoates

Polyhydroxyalkanoate (PHA) polyesters are degradable, biocompatible, thermoplastic materials made by several microorganisms. They are intracellular storage polymers whose function is to provide a reserve of carbon and energy. PHB and it copolymers with up to 30% of 3-hydroxyvaleric acid are now commercially available under the trade name Biopol.

Degradable tyrosine-polycarbonates are an other important polymer for cell adhesion and tissue engineering.

Poly(α-Hydroxy Acids)

Naturally occurring hydroxy acids, such as glycolic, lactic, and ε-caproic acids, have been utilized to synthesize an array of useful biodegradable polymers for a variety of medical product applications. As an example, bioresorbable surgical sutures made from poly(α-hydroxy acids) have been in clinical use since 1970; other implantable devices made from these versatile polymers (e.g. internal fixation devices for orthopedic repair) are becoming part of standard surgical protocol.

The final degradation and resorption of the poly(hydroxy acid) implants involve inflammatory response can have a deleterious effect on some healing events, these polymers have been successfully employed as matrices for cell transplantation and tissue regeneration.

Non-Biodegradable Polymers

Non-biodegradable polymers include polyacrylates, polymethacrylates, ethylene vinyl acetate, and polyvinyl alcohols. Polymers that can form ionic or covalently crosslinked hydrogels which are malleable—are used to encapsulate cells. A hydrogel is a substance formed when an organic polymer (natural or synthetic) is cross-linked via covalent, ionic, or hydrogen bonds to create a three-dimensional open-lattice structure which entraps water molecules to form a get.

Examples of materials which can be used to form a hydrogel include polysaccharides such as alginate, polyphosphazines, and polyacrylates, which are crosslinked ionically, or block copolymers such as Pluronics' or Tetronics', polyethylene oxide-polypropylene glycol block copolymers which are crosslinked by temperature or pH, respectively. In general, these polymers are at least partially soluble in aqueous solutions, such as water, buffered salt solutions, or aqueous alcohol solutions, that have charge a side groups, or a monovalent ionic salt thereof. Examples of polymers with acidic side groups that can be reacted with cations are poly (phosphazenes), poly(acrylic acids), poly(methacrylic acids), copolymers of acrylic acid and methacrylic acid, poly (vinyl acetate), and sulfonated polymers, such as sulfonated polystyrene.

Copolymers having. acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups. Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Examples Scaffolds and their Preparation

There have been performed some experiments for the preparation of foam-like scaffolds:

PLLA dissolved in $CH_2Cl_2$ cast over non woven PGA fibers evaporation and vacuum drying heating over m.p. PGA quenching, cooling selective dissolving PLLA by $CH_2Cl_2$.

Spraying of rotating PGA—mesh by PLLA

Solvent casting and leaching of the porogen:

Salt (sugar) particles dispersed in PLLA microstructures/ $CHCl_3$-solution casting, drying water leach out the salt Melting salt—PLLA—mixtures PLGA blending with PEG soft Tissue application PLLA soaking in PVA Extrusion composite wafers with NaCl leached out
Printing: 3-D Printing—Incorporation salt into the Powder Emulsion—freeze drying process water to PLGA in $CH_2Cl_2$ Emulsed freeze dryed 20-30 μm pores
PLLA in glacial acid frozen −10° C. drying (1 week)
Polymer-ceramic: NaCl+Hydroxyapatite in PLGA-solution in $CHCL_3$ water-PVA-solution to emulsion dried leached
Hydroxyapatite-powder to PLGA dioxene solution freeze dried Preferably the solvent casting of PLLA is used with dispersed NaCl particles, which can be leached out by water forming interconnecting pores of 50-300 μm.

Other polymers used for biodegradable foam forming:
Polyhydroxybutyrat and copolymers
Biopol
Polydioxanone
Poly (ε)-caprolactone
Polyorthoesters
Polyanhydrides (F-K-Gliadel)
Polyphosphazene
Polyaminoacids
Polyaminocarbonat-polyaminoocarbonat-tyrosine
Mixtures thereof.

Periodontitis

Periodontitis is a disease that results in the destruction of supporting tissues of the teeth, subsequent gingival pocket formation, and ultimately tooth loss. The main etiology is bacterial infection, but occlusal and systemic disorders are considered aggravating factors. Although periodontitis is not life threatening, it is one of the most widespread disorders found among human populations. Most surveys in Europe state that more than 40% of persons in the age group of 35-45 years old present periodontal pocketing. The periodontal status deteriorates as the subjects grow older: In France the percentage of people with periodontal exceeds 60% in the age group 45-64 years old. In the United States 36% of the population 19 years and older presents periodontitis; this increases to 52.20% of persons 45-64 years old). Health costs for this disease have been estimated at $5-6 billion involving 120-133 million hours of treatment, even though most patients do not seek treatment.

Initial concern was in arresting the evolution of the disease after restoring last periodontal material. For several decades, periodontists have been striving to regenerate destroyed periodontium. Among earlier attempts, curettage, open-flap debridment, and diverse bone grafting procedures can be cited. These therapeutic modalities most often result only in

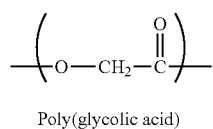
Poly(glycolic acid)

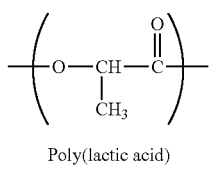
Poly(lactic acid)

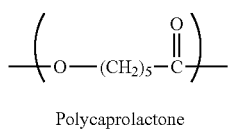
Polycaprolactone

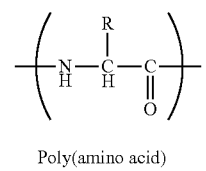
Poly(amino acid)

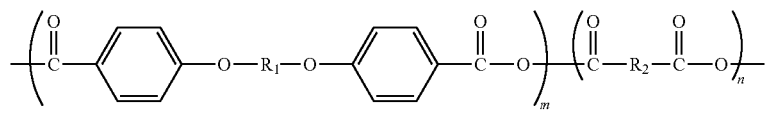
Polyanhydride

Poly(ortho ester)

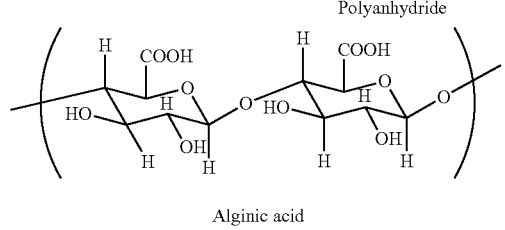
Alginic acid

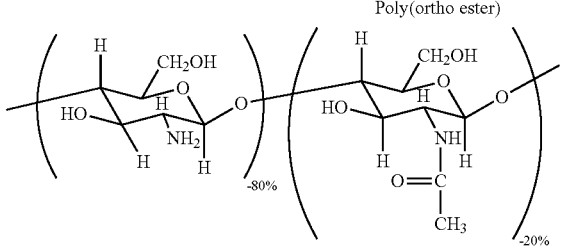
Chitosan

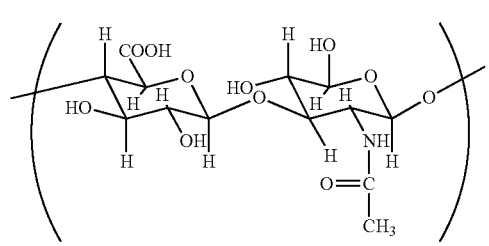
Hyaluronic acid partial repair and in residual pockets, primarily because progenitor cells of highly specialized tissues are not easily secured but also because of the particularly difficult wound closing conditions pertaining to periodontal surgery. As in type of wound, a blood clot is formed very rapidly. In dermal wounds, fibrin bridging is sufficient to close the wound, and epithelial proliferation, which starts within 24 hr, is limited to the epidermal lesion. In periodontal lesions, the gingival can bind only to the vascular surface of the teeth, and very often the adherence is too frail, or the blood clot is resorbed too rapidly. In this case, a long junctional epithelium may develop, between the tooth and the flap, resulting in the formation of a pocket. An additional complication is the accumulation of plaque. Oral microorganism adhere to the portion of the tooth surface that is next to the marginal gingival. Because of these wound closure hindrances, complete submersion of the teeth under gingival flaps has been advocated but in seldom feasible in human clinical situations.

New advances in periodontal therapy include the use of membrane barriers to guide the regenerative tissue, and implantation of bone substitutes. These techniques apply to vertical bone lesions and are becoming quite efficacious and predictable. Promoting regeneration at a distance from a potential source of osseous cell remains difficult, but better knowledge of cheramoattractants, growth factors, and osteoinduction proteins is likely to help to develop clinical applications that enhance healing and facilitate the selection of proper cell populations for bone or gingival reconstruction. The introduction of teeth derived stem cells for vascularization, regeneration periodontal tissue, gingival tissue and bone is an important step for improvement of guided tissue regeneration.

Guided Tissue Regeneration

Tissue Regeneration is an important field for regeneration processes improved by stem cells and s.c. derived or stimulated cell lines. the presence of gingival is detrimental to the regeneration of the attachment apparatus. However, Nyman and co-workers were the first to find an effective way of excluding gingival epithelial and connective tissue cells from reconstruction sites. Their initial attempt to regenerate periodontium in the human succeeded in forming 5 mm of new attachment with collagen fibers embedded in cementum. They used a Millipore filter, which served as a barrier to keep connective tissue cells out of the resorbed site and avoid downward growth of the gingival epithelium along the root surface. Little bone was produced, perhaps because the filter collapsed against the tooth. Soon after, another material was adopted: expanded poly(tetrafluoroethylene) (e-PTFE), or Teflon. The advantages of e-PTFE are its stiffness, that it allows more room for bone formation, is biocompatible, and the ease with which it can be removed. Numerous studies have proved the ability of e-PTFE membranes to promote repair of intrabony and furcation defects. Histologic confirmation of the repair, evidencing neoformation of cementum, periodontal ligament, and alveolar bone, was obtained in both humans and animals). The material has, however, two major drawbacks: it causes severe gingival recession and, once exposed, accumulates large amounts of bacterial plaque. Vascularization of the marginal gingival is provided solely by terminal capillaries. The placement of a cell-tight barrier disturbs the blood supply and avoids endothelial anastomosis with blood vessels originating from the underlying tissues. Bacteria actively proliferating in the crevicular part of the tooth will then colonize the e-PTFE membrane. Because of the subsequent inflammation, the Teflon membrane must be removed between 4 and 6 weeks after replacement). To avoid the requirement for second-stage membraneretrieval and to minimize bacterial infection, resorbable membranes have been developed using collagen or polysaccharide polymers. Collagen membranes used experimentally can be made from rat-tail, bovine dermis, or other sources. Industrially produced collagen membranes include collagen from calf endocardium and are in use in human clinics. Different types of poly(lactic acid), poly(galactic acid) or a novel product dissolves lactic acid in N-methyl-2-pyrolidone have been used to form polymer membranes. When exposed, resorbable membranes accumulate small amounts of bacterial plaque because bacterial and salivary enzymes accelerate their resorption. Thus permeabilized, the membrane is partially protected by the tissue exudates. Many polymer barriers feature pores that allow fluid circulation or even alimited amount of tissue ingrowth. The resorption rate of resorbable barriers can modulated and thus their effect prolonged if needed. How long a membrane should stay in place has not been determined.

Although membranes exclude gingival tissue they do not enable the selection of periodontal ligament cells or bone cells. It was first postulated that periodontal ligament cells were the slowest to migrate. This was supported by experiments showing that after injury the proliferation of periodontal ligament cells peaked at 2 or 3 days. It was suspected that this apparently limited proliferation was caused by a weak angiogenesis and that premature differentiation delayed migration). Periodontal ligament cells migrated several millimetres along the implant, producing cementum and a periodontal-like ligament. The cells were able to colonize a fairly large surface much faster than the osseous cells crossed the minute space left by the drill. It seems then that these two types of cells do not compete, but primarily restore their intended functions. Whether resorbable or made of e-PTFE, membranes should be positioned under the flap margin. The appropriate use of barrier membranes promotes predictable osseous repair and histologically verifiable new attachment with neoformation of cementum and periodontal ligament fibers. In this point of view the transplantation of Stem Cells derived from follicle cells can enforce remodelling of periodontium.

Bone Substitutes

Intraoral autologous bone grafts are, of course, choice material when osseous defects need to be repaired. However, intraoral autologous bone is not always available in sufficient quantities, particularly when patients present a deficiency of alveolar bone resulting from severe periodontitis.

Bone substitutes include synthetic materials such as hydroxyapatite and methyl methacrylate, and modified mineralised biologic substances such as coralline or bovine trabecular bone and lyophilised human bone. These products provide surgical ease and patient comfort, and their various resorption rates are interesting. Opponents of bone grafting techniques affirm that regeneration of the periodontal attachment apparatus is not achievable by, or at least has not been evidenced for, procedures other than membranes implantations). The best results were obtained when teeth were submerged under flaps or when the sites were protected from epithelial downward growth by gingival grafts). Bone substitutes have been suspected to impair the regeneration of connective tissue attachment. Periodontal ligament cells are capable of covering blocks hydroxyapatite embedded in root surfaces and subsequently secreting cementum on synthetic material. Production of this newly formed connective attachment with inserted collagen fibers is slightly delayed compared to regeneration on natural dentine surfaces. It is sometimes postulated that new attachment occurs preferentially where new bone is present. All techniques that enhance bone formation would then be beneficial to connective attachment regeneration. Research by Lowenguth et al. (1993) exposed a factor that may be important for engineering teeth. They implanted surface-demineralized dentine cylinders in rat skin and observed that appropriate approximation of dentine surfaces enhanced the orientation of fibroblasts and collagen fibers perpendicular to the walls of the cylinders. The customary use of bone substitutes has been in infrabony pockets (Yukna, 1994a) and alveolar ridge preservation (Greenstein et al., 1985), but this presents some limitations. If resorbable, the substances can be resorbed by the gingival. The material can also cause necrosis of the papillar and gingival tissue covering the defects. In such cases the bone substitute is lost and the defect is even harder to treat. Therefore, in spite of the fact that bone substitute may induce great amounts of bone repair. Proponents of the membrane techniques often admit that barriers alone do not include the formation of much alveolar bone, or at least not above the existing crestal level. Only bone grafting techniques with bone or substitute materials promote the formation of a new bone, cementum, and periodontal ligament coronal to the ridge (Yukna, 1994b). It may be possible to generate mandibular/maxilar bone by seeding stem cells derived from follicle cells into the bone of patients.

Growth Factors for periodontal Tissue Engineering

Fibronectin has been considered a promising promoter of fibroblastic activity. and that topical application of fibronectin on demineralized roots could be beneficial to healing. fibroblast growth factor (FGF) has a potent chemotactic effect on fibrobalsts derived from periodontal ligament tissues. FGF is 10.000 time more powerful than fibronectin in inducing fibroblast growth. Platelet-derived growth factor (PDGF) is another chemoattractant with great potential, and no amount of fibronectin can stimulate the proliferation of periodontal ligament fibroblasts to the extent achieved by nanograms of PDGF The usefulness of fibronectin can also be questioned, because it has been shown that it enhances the migration of basal keratinocytes (Where epithelial cells colonize the root before connective tissue is formed, there will be no attachment apparatus. Therefore, although fibronectin attracts and orients fibroblasts properly, some of its effects might not be desirable. Plasmatic protein sealants containing large quantities of fibrinogen, but also fibronectin and coagulation factors, have been used with success to avoid suturing, but very moderate gains in attachment levels when fibronectin was applied on demineralised root surfaces. Biologic glues have also been proposed as spacers to keep membrane barriers at a distance from the roots, but the usefulness of fibrinogen and/or fibronectin in periodontal surgery is still inconclusive—It is possible to put stem cells into biological glue.

FGF and PDGF both have powerful effects on periodontal ligament fibroblasts. Periodontists have also shown interest in transforming growth factor β (TGF-β; which appears to promote more significant deposition of fibroblast collagen than any of the other growth factors, although it is not a fibroblast chemoattractant. The combination of FGF and insulin-like growth factor (IGF-1) seems promising as well, promoting the same collagen deposition as TGF-β and a greater proliferation of ligament fibroblasts than PDGF alone). The PDGF-IGF-1 combination is chemotactic and mitogenic for periodontal fibroblasts; PDGF is chemotactic for osteoblasts, and promotes the synthesis of noncollageneous proteins in bone cultures, and IGF-1 promotes the synthesis of collagen proteins.

The PDGF-IGF-1 combination results in greater bone matrix formation than any individual growth factor, and interacts synergistically to yield significant collagen formation and healing in soft tissue wounds). The delivery of growth factors through a gel allows the presence of a great amount of PDGF and IGF-1 during a short period of time, and even better results could perhaps be obtained with a slow-release system. Repair requires several weeks and it will be interesting to develop acceleration with Stem Cells slow-release devices. Bone morphogenic proteins (BMPs), a mixture of peptides initially identified as a bone growth factor and later shown to comprise at least 13 individual proteins can promote new bone formation at the site of implantation, instead of changing the bone growth rate of existing bone. BMPs induce mesenchymal precursor cells to differentiate in cartilage and in bone-forming cells. Thus, with recombinant human bone morphogenic protein 2 (rhBMP2), the proximity of residual bone is less important for osseous formation. RhBMP in a carrier enhances periodontal regeneration. The membrane favors migration and proliferation of already RhBMP promotes the grouping of mesenchymal stem cells in clusters, later developing in appropriate tissues. RhBMP may promote vertical bone formation in horizontal osseous defects. The abundant bone produced not only covered the denuded half-root but some cases even grew over portions of the crowns of the teeth. A small 12.5-kDa peptide), PDL-CTX, also seems to be a potent chemoattractant for periodontal ligament cells, with mitogenic properties or cells in early stages such as stem cells. The growth factor amelogenin, found in the epithelial cells forming the enamel organ, has been extracted from pigs and results in neoformation of a acellular cementum. Amelogenin increases proliferation of ligament fibroblasts but not of epithelial cells. Amelegenin is a potent promotor for stem cell derived tissue engineering.

Regeneration of Dentin

It may be possible to induce the differentiation of odontoblasts from pulp tissue using certain bone morphogenetic proteins and thereby induce the synthesis of new dentin or stem cells derived from the dental pulp (Gronthos et al. 2000). It may be also possible to implant teeth derived stem cells into dentin. Successful development of a process to engineer successfully the regeneration of dentin could have commercial applications as an enhanced pulp capping agent, as an alternative to root canal therapy under certain circumstances, and as a potential means of reducing tooth sensitivity often associated with the placement of tooth fillings.

Dentin Powder may be used as dentinogenial transmitter substance for seeding stem cells. Crude dentin fractions prepared by ethylenediaminetetraacetic acid (EDTA) extraction and collagenase digestion stimulate reparative dentinogenesis. in small pulp exposures in ferrets or reactive dentinogenesis when applied to freshly cut dentin surfaces. Some extracellular matrix component is a prerequisite to odontoblast differentiation and tubular dentin formation. To regulate odontoblast differentiation and hence the architecture of the tissue may possible by stem cells implantation. Regulation of dentin architecture may be important.

Dental Lamina

Within the dental lamina, continued and localized proliferative activity leads to the formation of a series of epithelial ingrowths into the ectomesenchyme at sites corresponding to the positions of the future deciduous teeth. At this time the mitotic index, the labelling index, and the growth of the epithelial cells are significantly lower than corresponding indices in the underlying ectomesenchyme, which suggests that part of the "ongrowth" is achieved by ectomesenchymal upgrowth. From this point tooth development proceeds I three stages: the bud, cap, and bell. These terms are descriptive of the morphology of. the developing tooth germ; they do not properly describe the significant functional changes that occur during development, such as morphogenensis and histodifferentiation. It should also be noted that, because development is a continuous process, clear distinction between the transition stages is not possible. A further problem for the beginning student is that in examining sections of human embryos it is possible to section a tooth germ at a particular stage of development in such a way that it mimics another (FIG. 6-4)

Vascular Supply

Clusters of blood vessels are found ramifying around the tooth germ in the dental follicle and entering the dental papilla (or pulp) during the cap stage. Their number in the papilla increases during histodifferentiation, reaching a maximum at the onset of the crown stage of tooth development. Interestingly, the vessels entering the papilla are clustered into groups that coincide with the position where the roots will form. With age, the volume of pulpal tissue diminishes and the blood supply becomes progressively reduced, affecting the tissue's viability.

The dental organ, derived solely from epithelium, is avascular, although a heavy concentration of vessels in the follicle exists adjacent to the outer dental epithelium.

EXAMPLES

Tissue Engineered on Biodegradable Polymer Scaffolds

We fabricated biodegradable scaffolds in the shape of human molars, seeded them with stem cells derived from stem cells cultured in D-MEM serumreplacement media (GIBCO/BRL) supplemented with 2 mM L-glutamine/100 units/ml penicillin/100 µg/ml streptomycin. (Biofluids, Rockville, Md.), and implanted the cell/polymer constructs in a cell rotation reactor type from Synteon, Rotary Cell Culture System RCCS-D, with 50 ml vessel (D-405). A microporous PLLA cell/polymer construct isolated 6 weeks post-implantation had a cell layer adjacent to the polymer.

Our approach. for future therapeutic application is the transplantation of resorbable polymeric scaffolds colonized with stem cells for the periodontium or bone tissue.

We investigated biochemical and physicochemical parameters of two different polylactid polymer matrices (PLLA, RG 207 Boehringer Ingelheim FRG): biocompatibility, growth of periodontal cells, degradation kinetics and available capacities of modifying steps which porosity has been induced by salt leaching.

Using in vitro cytotoxicity assays, both of the prototypes have been proven as non toxic, regarding primary cultivated fibroblasts. Cellular adhesion and proliferation as well as specificity have been ascertained on fixed sections of the cultured scaffolds by microscopic techniques (FIG. 8). Concerning a potential clinical application, the polymer sponge has due to its structural properties to additional option of a drug release system.

FIG. 8 shows a fixed section of scaffold with cultured stem cells (stained with Hoechst 33258)

Stem Cells Derived From Teeth

FIG. 9 shows pore structure of PLLA-polymer (80× magnification)

TABLE 1

| |
|---|
| PLLA cast over non woven PGA fibers |
| PGA-mesh by PLLA |
| PLLA microstructures |
| PLGA blending with PEG |
| PLLA soaking in PVA |
| Printing: 3-D Printing |
| Emulsion-freeze drying process |
| Polymer-ceramic: Hydroxyapatite in PLGA-PVA |
| Hydroxyapatite PLGA |
| Polyhydroxybutyrat and copolymers |
| Biopol |
| Polydioxanone |
| Poly (ε)-caprolactone |
| Polyorthoesters-polythyrosine-carbonates |
| Polyanhydrides (F-K-Gliadel) |
| Polyphosphazene |
| Polyaminoacids |
| Polyaminocarbonat-polyaminoocarbonat-tyrosine |
| Photopolymers |
| Mixtures thereof. |

TABLE 2

| |
|---|
| A matrix having cadherins enhancing the binding of homophilics |
| A matrix having cadherins enhancing the binding of heterophilics which are lectins-like e.g. branched Oligosaccharide structures namely the sialyl X and A structures |
| A matrix having the immunglobuline family, proteins that are denoted as cell adhesion molecules (CAMs) for homophilic and heterophilic binding |
| A matrix having integrins, dimeric molecules, consisting of the α and β subunit for cell-cell and for cell-matrix-binding (collagen, fibronectin, vitronectin, vWF, and lamin). |

Appendix

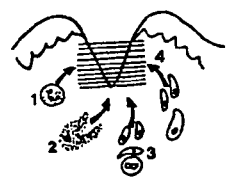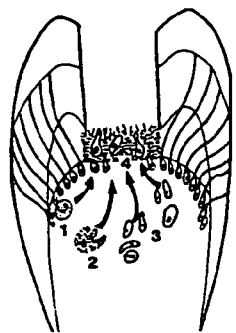

Left

Comparison of the repair responses in skin and teeth. There is no epithelial response in teeth, but the connective tissue response is similar in both instances and involves (1) polymorphs, (2) macrophage, (3) fibroblasts (by division of undamaged pulpal and perivascular cells), and (4) the production of scar tissue (collagen), which mineralizes in the tooth to form dentin.

For therapeutic approaches it seems to be prudent to implant stem cells from teeth into dentin for improved healing of caries.

Right

Repair response after tooth extraction. A shows the tooth in situ. After extraction the socket, B, is filled with clot. The clot resolves, C, by (1) the polymorph response, (2) the macrophage response, and (3) the fibroblast response. In addition, the bony defect becomes colonized by new osteoblasts (4) that remodel the collagen scar and form bone, D.

In a follow up of the present invention, it is possible to introduce a crude tooth engineered from stem cells into the socket during forming of the clot.

In any stage of healing of periodontium it is prudent to implant stem cells derived from teeth with or without a polymeric matrix into the wound bed.

Implantation of stem cells derived from teeth are able to regenerate periodontium in any stage of healing (a-d) with and without a guiding scaffold(Membrane)

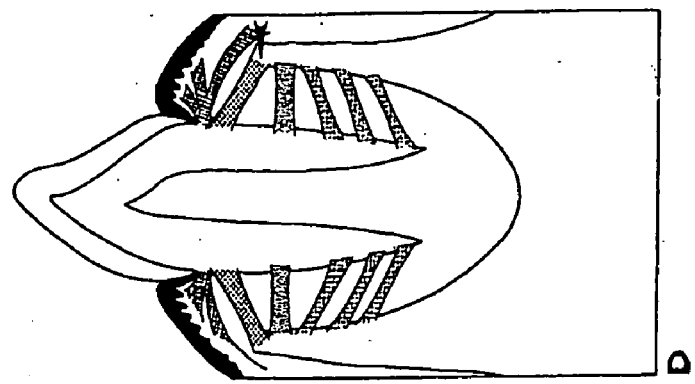
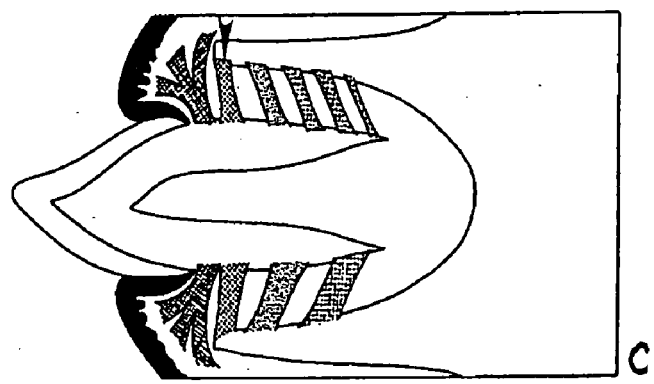
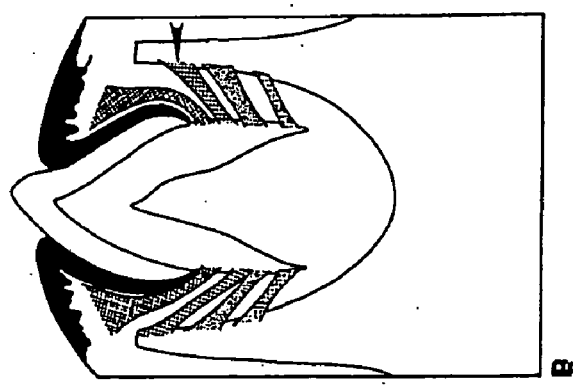
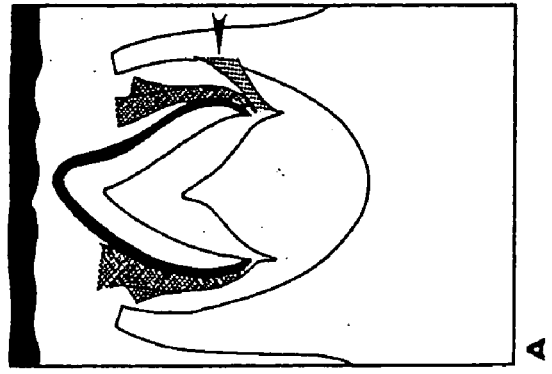

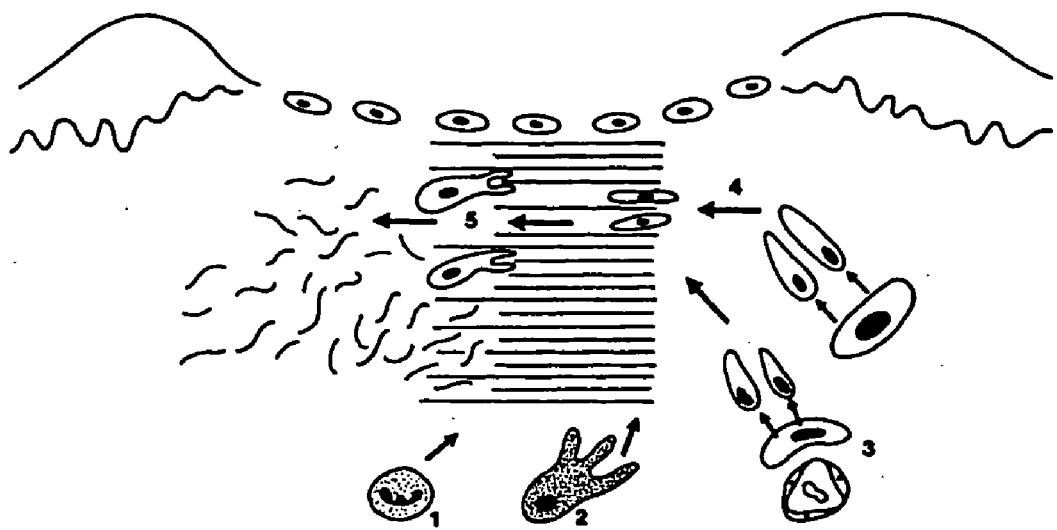

Summary of gingival tissue repair. The epithelial response is achieved by proliferation and migration of cells to cover the defect. The connective tissue response involves successively (1) a polymorph response (12 to 24 hours), (2) a macrophage response (2 to 5 days), and (3) a fibroblast response (2 days and on) from undifferentiated perivascular cells and undamaged fibroblasts. The new fibroblasts (4) form the collagen of scar tissue.

For improvement of wound healing, it is possible to introduce stem cells from teeth into the wound bed.

Repair in gingival epithelium illustrating why scars are rare in the mouth. The repair process up to step 4 is as depicted in FIG. 18-7 involving (1) the polymorph response, (2) the macrophage response, (3) fibroblast differentiation, and (4) collagen synthesis. The scar remodels (5) by collagen phagocytosis.

REFERENCES

Civin, C. I., L. C. Strauss, et al. (1984). J Immunol 133(1): 157-65.
Friedenstein A 3, Gorskaja U, Kalugina N N (1976) Exp. Hematol. 4: 267-274
Greenstein, G., R. A. Jaffin, et al. (1985). J Periodontol 56(4): 200-3.
Gronthos S, Mankani M, Brahim 3, Robey P G, Shi S. (2000) Proc Natl Acad Sci USA
Harada H, Kettunen P, lung H—S, Mustonen T, Wang Y A, Thesleff I (1999) J. Cell Biol. 147:10
Johansson, C. B., M. Svensson, et al. (1999a). Exp Cell. Res 253(2): 733-6.
Johansson C B, Momma S, Clarke D L, Risling M, Lendahl U, Frisen I (1999b) Cell
Lowenguth, R. A., A. M. Poison, et al. (1993). 3 Periodontol 64(5): 330-42.
Pittenger, M. F., A. M. Mackay, et al. (1999). Science 284 (5411): 143-7.
Sigurdsson, T. J., M. B. Lee, et al. (1995). J Periodontol 66(2): 131-8.
Sharpe (2000) (WO 01/60981)
Shi S, Gronthos S, Robey P G. WO 02/07679
Ten Cate, Oral Histology, Fifth Ed., Mosby Inc. 1998
Vierck, J. L., J. P. McNamara, et al. (1996). In Vitro Cell Dev Biol Anim 32(9): 564-72.
Winer J. Jung C K, Shackel I, Williams P M. Anal Biochem (1999) 270:41-49

---

The invention claimed is:

1. A method for obtaining an isolated dental follicle stem cell said method comprising the steps of taking cells from tissue surrounding the epithelial enamel organ of a human tooth (dental follicle), culturing the taken cells, and isolating a plastic adherent cell from the cell culture, wherein the plastic adherent cell (i) self-renews, (ii) differentiates into cells of endodermal, mesodermal, or ectodermal lineage, (iii) expresses markers nestin, notch-I, and vimentin, but is devoid of markers CD34 and CD133, (iv) differentiates in vitro in the presence of dexamethasone into a tissue-like structure comprising calcium deposits, and (v) builds a calcium-containing follicle-tissue membrane when stimulated with dexamethasone in vitro.

2. An isolated human dental follicle stem cell, wherein the stem cell (i) self-renews, (ii) differentiates into cells of endodermal, mesodermal, or ectodermal lineage, (iii) expresses markers nestin, notch-I, and vimentin, but is devoid of markers CD34 and CD133, (iv) differentiates in vitro in the presence of dexamethasone into a tissue-like structure comprising calcium deposits, and (v) builds a calcium-containing follicle-tissue membrane when stimulated with dexamethasone in vitro.

3. A method for producing a dental follicle clonal stem cell line comprising the steps of
   a) isolating a single dental follicle according to claim 1 and
   b) culturing and expanding the isolated stem cell to generate a clonal population.

4. A dental follicle clonal stem cell line obtainable by the method of claim 3, wherein the dental follicle stem cells contained therein (i) self-renew, (ii) differentiate into cells of endodermal, mesodermal, or ectodermal lineage, (iii) express markers nestin, notch-I, and vimentin, but are devoid of markers CD34 and CD133, (iv) differentiate in vitro in the presence of dexamethasone into a tissue-like structure comprising calcium deposits, and (v) build a calcium-containing follicle-tissue membrane when stimulated with dexamethasone in vitro.

5. A method of producing a genetically engineered dental follicle stem cell comprising the steps of
   a) introducing a DNA construct comprising at least one of a marker gene or a gene of interest into an isolated dental follicle stem cell of claim 2;
   b) selecting a stem cell for expression of the marker gene or gene of interest; and
   c) culturing the selected stem cell.

6. A genetically engineered stem cell obtainable by the method of claim 5, wherein genetically engineered stem cell (i) self-renews, (ii) differentiates into cells of endodermal, mesodermal, or ectodermal lineage, (iii) expresses markers nestin, notch-I, and vimentin, but is devoid of markers CD34 and CD133, (iv) differentiates in vitro in the presence of dexamethasone into a tissue-like structure comprising calcium deposits, and (v) builds a calcium-containing follicle-tissue membrane when stimulated with dexamethasone in vitro.

7. A method for culturing a dental follicle stem cell of claim 2 in a medium containing one substance for differentiation selected from the group consisting of insulin, retinoic acid, indomethacin, 1-methyl-3-isobutylxanthine theophylline, a transforming-growth-factor-β, a bone morphogenetic protein, a fibroblast growth factor, an epidermal growth factor, a platelet derived growth factor, a vascular endothelial growth factor, hepatocyte growth factor, an interferon, an insulin-like growth factor, an interleukin, nerve growth factor, and a combination thereof.

8. The stem cell according to claim 2, which is capable of differentiating into a periodontal ligament structure.

9. A culture comprising
   a) the stem cell according to claim 2 and
   b) a medium capable of supporting proliferation of the stem cell or a medium comprising dexamethasone to differentiate the stem cell into a biological membrane.

10. A pharmaceutical composition comprising:
    a) a stem cell according to claim 2; and
    b) a pharmaceutically acceptable medium or carrier.

11. The pharmaceutical composition of claim 10 further comprising a proliferation factor or lineage commitment factor.

* * * * *